(12) United States Patent
Maeda et al.

(10) Patent No.: US 10,561,819 B2
(45) Date of Patent: Feb. 18, 2020

(54) CATHETER

(71) Applicant: TERUMO KABUSHIKI KAISHA, Shibuya-ku, Tokyo (JP)

(72) Inventors: Naoyuki Maeda, Odawara (JP); Yuuki Souma, Odawara (JP); Ryota Takeuchi, Sapporo (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 298 days.

(21) Appl. No.: 15/429,604

(22) Filed: Feb. 10, 2017

(65) Prior Publication Data
US 2017/0151415 A1 Jun. 1, 2017

Related U.S. Application Data

(63) Continuation of application No. PCT/JP2015/074623, filed on Aug. 31, 2015.

(30) Foreign Application Priority Data

Sep. 4, 2014 (JP) .................. 2014-180039
Sep. 4, 2014 (JP) .................. 2014-180050
Sep. 4, 2014 (JP) .................. 2014-180067

(51) Int. Cl.
*A61M 25/10* (2013.01)
*A61M 25/00* (2006.01)
(Continued)

(52) U.S. Cl.
CPC ......... *A61M 25/0052* (2013.01); *A61B 17/22* (2013.01); *A61M 25/0108* (2013.01);
(Continued)

(58) Field of Classification Search
CPC .......... A61M 25/10; A61M 2025/1075; A61M 2025/1084
See application file for complete search history.

(56) References Cited

U.S. PATENT DOCUMENTS 4,796,629 A * 1/1989 Grayzel .............. A61M 25/104
604/103.09
5,647,848 A * 7/1997 Jørgensen ........... A61M 25/104
604/103.11
(Continued)

FOREIGN PATENT DOCUMENTS

JP 2008-501408 A 1/2008
JP 2008-253800 A 10/2008
(Continued)

OTHER PUBLICATIONS

International Search Report (PCT/ISA/210) dated Nov. 24, 2015, by the Japanese Patent Office as the International Searching Authority for International Application No. PCT/JP2015/074623.
(Continued)

*Primary Examiner* — Ryan J. Severson
(74) *Attorney, Agent, or Firm* — Buchanan Ingersoll & Rooney PC

(57) ABSTRACT

A catheter including a balloon. The balloon has an elastic inner layer and an elastic outer layer. The inner and outer layers are tubular and are inflatable and deflatable in response to a change of internal pressure of the balloon. The catheter includes a tubular reinforcement member positioned radially between the inner layer and the outer layer. The reinforcement member has a first end portion and a second end portion opposite the first end portion in the axial direction of the catheter. The reinforcement member has an intermediate portion between the first end portion and the second end portion in the axial direction. At least one of the first and second end portions is not directly fixed to both the inner layer and the outer layer. The intermediate portion is not directly fixed to both the inner layer and the outer layer.

20 Claims, 19 Drawing Sheets

(51) Int. Cl.
    *A61B 17/22*     (2006.01)
    *A61M 25/01*     (2006.01)
    *A61M 25/09*     (2006.01)
    *A61M 29/02*     (2006.01)

(52) U.S. Cl.
    CPC .......... *A61M 25/09* (2013.01); *A61M 25/104* (2013.01); *A61M 25/1029* (2013.01); *A61M 29/02* (2013.01); *A61B 2017/22001* (2013.01); *A61B 2017/22051* (2013.01); *A61M 2025/0183* (2013.01); *A61M 2025/1075* (2013.01); *A61M 2025/1079* (2013.01)

(56) References Cited

U.S. PATENT DOCUMENTS

| | | | | |
|---|---|---|---|---|
| 7,354,419 | B2* | 4/2008 | Davies, Jr. | A61M 25/104 604/103.06 |
| 7,682,335 | B2* | 3/2010 | Pepper | A61L 29/085 604/103.13 |
| 8,349,237 | B2* | 1/2013 | Horn | A61M 25/1029 264/257 |
| 8,697,212 | B2* | 4/2014 | Khieu | A61M 25/1029 428/36.2 |
| 8,715,229 | B2* | 5/2014 | Davies, Jr. | A61M 25/1029 604/103 |
| 8,858,855 | B2* | 10/2014 | Horn | A61M 25/1029 264/257 |
| 8,979,886 | B2* | 3/2015 | Campbell | A61L 29/085 606/192 |
| 9,144,666 | B2* | 9/2015 | Khieu | A61M 25/1029 |
| 9,211,391 | B2* | 12/2015 | Davies, Jr. | A61M 25/10 |
| 9,327,102 | B2* | 5/2016 | Aggerholm | B29C 49/04 |
| 9,457,170 | B2* | 10/2016 | Fujita | A61M 25/1029 |
| 9,526,873 | B2* | 12/2016 | Khieu | A61M 25/1029 |
| 9,713,657 | B2* | 7/2017 | Fujita | A61L 29/048 |
| 9,833,600 | B2* | 12/2017 | Stupecky | A61M 25/10 |
| 10,016,579 | B2* | 7/2018 | Campbell | A61M 25/10 |
| 10,099,039 | B2* | 10/2018 | Khieu | A61M 25/1029 |
| 10,105,522 | B2* | 10/2018 | Elton | A61M 25/104 |
| 2007/0250101 | A1* | 10/2007 | Horn | A61M 25/1029 606/192 |
| 2008/0033477 | A1* | 2/2008 | Campbell | A61L 29/085 606/194 |
| 2010/0042199 | A1 | 2/2010 | Burton | |
| 2011/0082489 | A1 | 4/2011 | Davies, Jr. et al. | |
| 2011/0172698 | A1 | 7/2011 | Davies, Jr. et al. | |
| 2013/0190690 | A1* | 7/2013 | Fujita | A61M 25/1029 604/103.06 |
| 2013/0253466 | A1* | 9/2013 | Campbell | A61M 25/10 604/500 |
| 2013/0261547 | A1 | 10/2013 | Aggerholm et al. | |
| 2014/0116606 | A1* | 5/2014 | Stupecky | A61M 25/10 156/229 |
| 2014/0207171 | A1* | 7/2014 | Fujita | A61L 29/048 606/192 |
| 2014/0336689 | A1* | 11/2014 | Elton | A61M 25/104 606/194 |
| 2015/0094658 | A1* | 4/2015 | Maeda | A61L 29/06 604/103.06 |
| 2017/0151415 | A1* | 6/2017 | Maeda | A61B 17/22 |
| 2017/0157368 | A1* | 6/2017 | Umeda | A61M 25/10 |
| 2017/0157373 | A1* | 6/2017 | Maeda | A61M 25/10184 |

FOREIGN PATENT DOCUMENTS

| | | |
|---|---|---|
| JP | 2014-518739 A | 8/2014 |
| WO | WO 96/040350 A1 | 12/1996 |
| WO | WO 2005/120622 A2 | 12/2005 |
| WO | WO 2012/167220 A1 | 12/2012 |

OTHER PUBLICATIONS

Written Opinion (PCT/ISA/237) dated Nov. 24, 2015, by the Japanese Patent Office as the International Searching Authority for International Application No. PCT/JP2015/074623.

The extended European Search Report dated Mar. 22, 2018, by the European Patent Office in corresponding European Patent Application No. 15838717.5-1132. (6 pages).

* cited by examiner

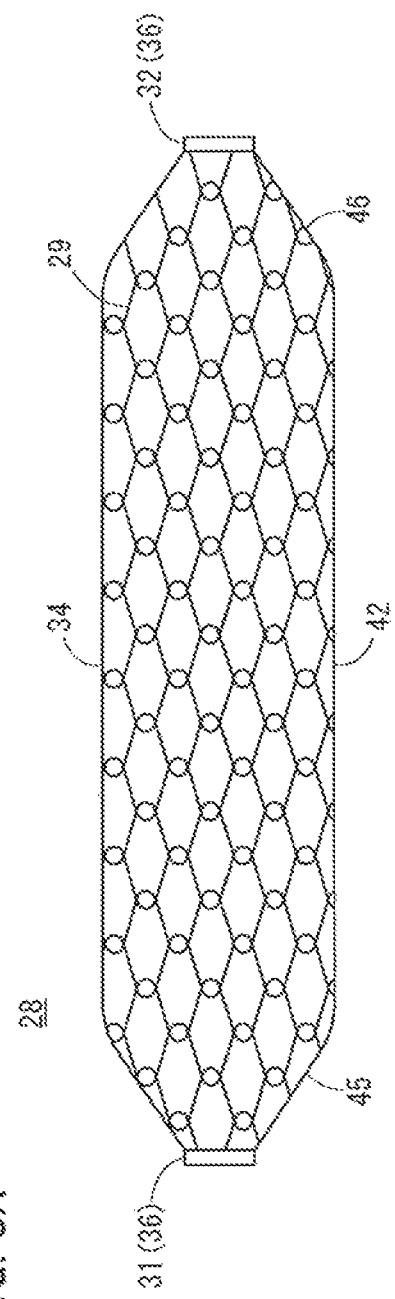
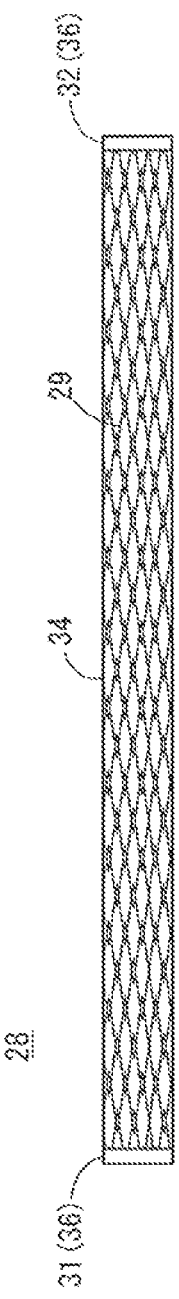
FIG. 3A
FIG. 3B

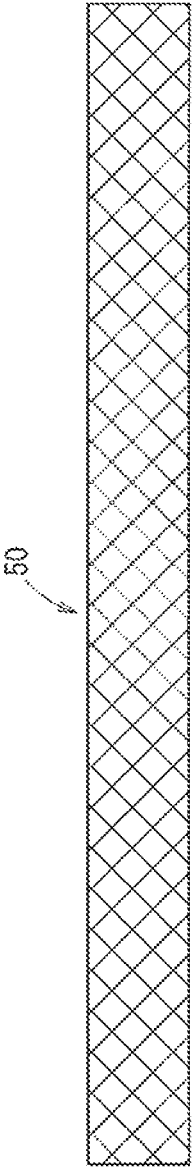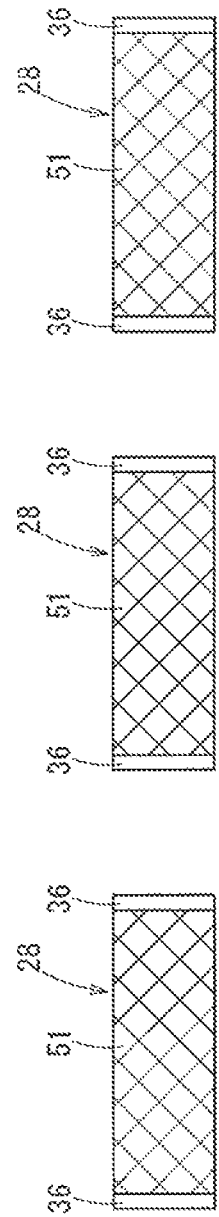

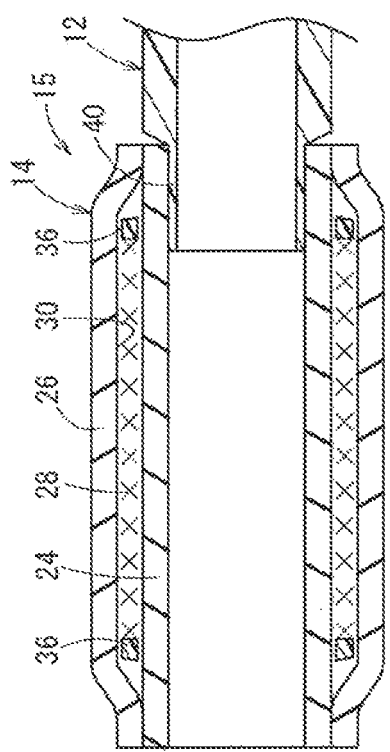
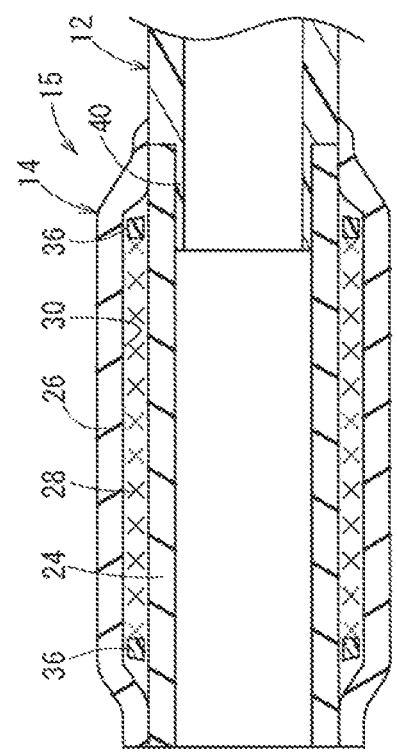
FIG. 7A
FIG. 7B

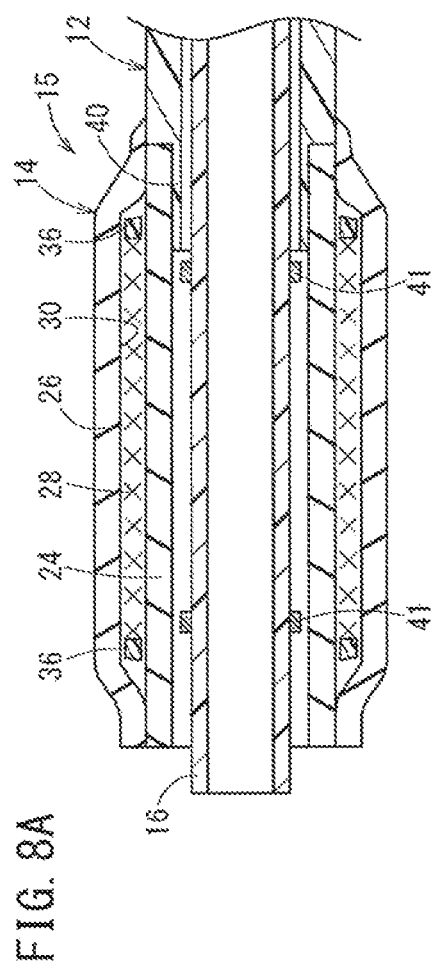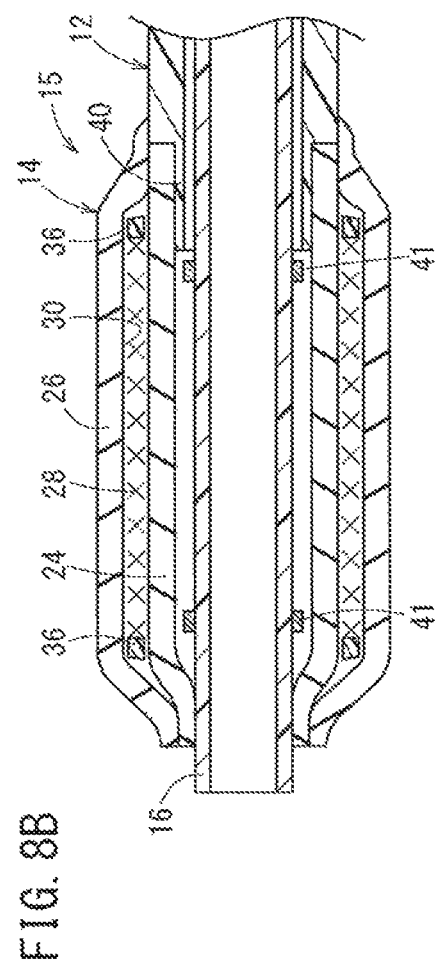

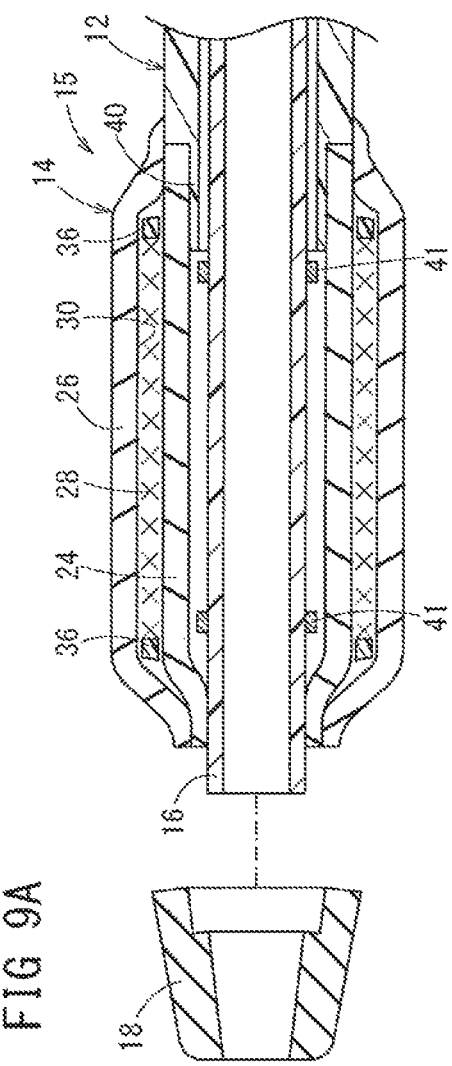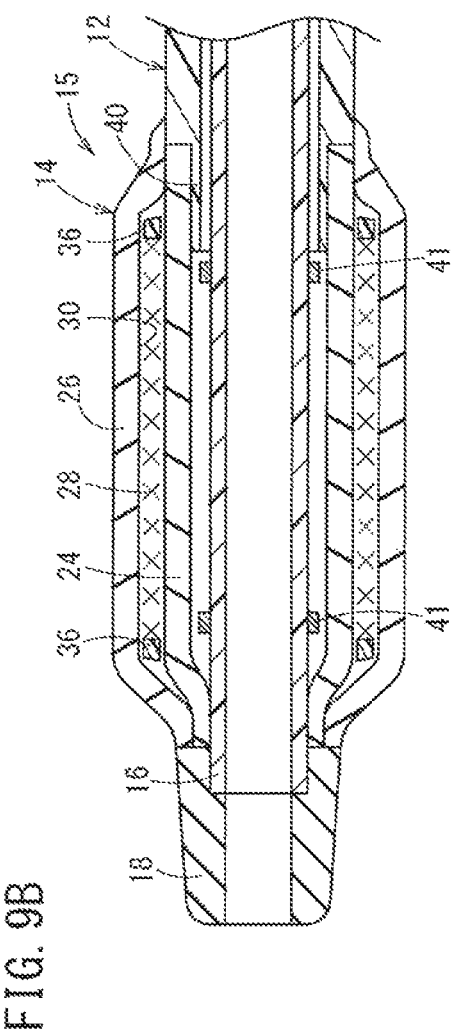

CATHETER

CROSS-REFERENCES TO RELATED APPLICATIONS

This application is a continuation of International application Ser. No. PCT/JP2015/074623 filed on Aug. 31, 2015, and claims priority to Japanese Patent Application No. 2014-180039, Japanese Patent Application No. 2014-180050 and Japanese Patent Application No. 2014-180067, which were each filed on Sep. 4, 2014. The entire content of these four patent applications is incorporated herein by reference.

TECHNICAL FIELD

The present invention generally relates to a catheter including a balloon reinforced with a reinforcement member.

BACKGROUND DISCUSSION

Recently, blood flow has been improved by widening a lesion (stenosed portion) of the coronary artery with a balloon catheter, in treatment of, for example, acute myocardial infarction and angina pectoris, percutaneous coronary intervention (percutaneous transluminal coronary angioplasty). For example, refer to Japanese Patent Application Publication No. 2008-501408. Treatment using a balloon catheter may also be performed to improve a lesion formed inside other blood vessels, the bile duct, the trachea, the esophagus, the urethra, and other body lumens.

Generally, a balloon catheter includes a long shaft and a balloon on the distal side of the shaft. The balloon inflates in the radial direction (i.e., expands radially outward by inflation). The balloon catheter is delivered to a stenosed portion in a body after a preceding guide wire is inserted through to the stenosed portion. When the balloon is positioned at the target stenosed site, the balloon is inflated by pressure-feeding an inflation fluid into the balloon. The stenosed portion can thus be widened.

In order to effectively treat a lesion area, the balloon of the balloon catheter is required to have sufficient strength to possess a desired balloon shape when being maximally inflated and to widen the lesion. Therefore, in order to apply high-pressure resistance, low compliance properties, and the like to a balloon, a configuration has been proposed in the related art in which a net-shaped reinforcement member is provided in a wall configuring the balloon. For example, refer to Japanese Patent Application Publication No. 2008-501408.

SUMMARY

A balloon catheter transports the balloon to a lesion inside the body lumen. Since the balloon needs to pass through the inside of the bent body lumen while being transported, the balloon is required to have flexibility (i.e., be flexible) to follow the bent state of the body lumen. The technology in the related art discussed above, in which a reinforcement member is provided in the wall of the balloon, has a problem in flexibility. The problem in flexibility arises because the reinforcement member is integrally fixed to the balloon, and there is no degree of freedom for movement relative to the wall of the balloon. It is thus difficult to apply sufficient flexibility to the balloon.

The catheter and catheter manufacturing method disclosed here have been made in consideration of such a problem. The catheter of this application thus possesses improved flexibility of a balloon reinforced with a reinforcement member, and this application discloses a method of manufacturing this improved catheter.

In order to achieve this improvement, the catheter disclosed here includes a balloon that has an inner layer and an outer layer. The inner and outer layers possess elastic stretching properties (i.e., are elastic), have tubular shapes, and are able to be inflated and deflated in response to a change of internal pressure. The catheter also includes a tubularly net-shaped reinforcement member positioned between the inner layer and the outer layer. The reinforcement member extends in an axial direction between a first end portion and a second end portion. The reinforcement member includes an intermediate portion between the first end portion and the second end portion. At least one of the first end portion and the second end portion, and the intermediate portion are not directly fixed to the inner layer and the outer layer. Here, the expression "at least one of the first end portion and the second end portion, and the intermediate portion are not directly fixed to the inner layer and the outer layer" denotes that at least one of the first end portion and the second end portion is not bonded to or embedded in the inner layer and the outer layer, and the intermediate portion is not bonded to or embedded in the inner layer and the outer layer, thereby being able to freely move inside a space formed between the inner layer and the outer layer.

Substantially the entirety of the reinforcement member has the degree of freedom for moving in the axial direction and a circumferential direction relative to the balloon. Therefore, favorable flexibility of the balloon can be maintained. Maintaining flexibility of the balloon improves the crossability (e.g., maneuverability) of the catheter inside a body lumen. Positioning the reinforcement member between the elastic inner and the outer layers of the balloon (i.e., layers with elastic stretching properties) allows for high-pressure resistance and low compliance properties to be suitably applied to the catheter. Here, the term "low compliance properties" denotes balloon characteristics when the balloon is inflated under high pressure such that the balloon diameter is not unlimitedly widened in response to the pressure and inflation under high pressure can result in a balloon with an appropriate/intended outer diameter. Moreover, the balloon is inflated and deflated while entailing elastic stretching and is a zero folding-type balloon (i.e., a balloon which is not folded when in the deflated state). Accordingly, the balloon can easily restore the original outer diameter when being deflated after inflation. Therefore, crossability (maneuverability) inside a body lumen can be further improved. An elastic balloon (i.e., a balloon having elastic stretching properties) can be prepared without performing blow molding. The catheter can be thus conveniently manufactured.

In the catheter, the other of the first end portion and the second end portion may also not be directly fixed to the inner layer and the outer layer. When both the first and second end portions are not fixed, the reinforcement member is not fixed to any one of the inner layer and the outer layer. Therefore, the degree of freedom for moving the reinforcement member relative to the inner layer and the outer layer of the balloon can be further improved and bending flexibility can be improved. This configuration allows for improved crossability inside a body lumen.

Inflation of the balloon at the first end portion and the second end portion in the circumferential direction may be restricted. The maximally inflated diameter of the intermediate portion of the reinforcement member positioned between the first end portion and the second end portion can thus be effectively restricted. The reinforcement member can thus suitably conduct the balloon reinforcing function.

The reinforcement member may be formed by tubularly knitting one or more threads. The waved (i.e., wavy or waved-shaped) threads adjacent to each other in the axial direction may be interlaced with each other. According to this configuration, the threads are folded in the circumferential direction when the reinforcement member is compressed in the circumferential direction, and the threads of the meshes become misaligned in the axial direction when the reinforcement member is compressed in the axial direction. Therefore, the reinforcement member can be flexibly bent.

The reinforcement member may be formed of a high-strength fiber possessing a tensile break strength equal to or greater than 2 GPa and an elastic modulus equal to or greater than 50 GPa. It is thus possible to realize a balloon having excellent high-pressure resistance and low compliance properties.

The axial-directional length of the reinforcement member may be greater than the axial-directional length of a region in the inner layer that is stretchable during deformation of inflation and deflation of the balloon. An axial-directional length of the outer layer may be greater than the axial-directional length of the reinforcement member. The maximally inflated diameters of the inner layer and the outer layer can be reliably restricted by positioning a reinforcement member of an appropriate length between the inner and outer layers.

The catheter may include a joint structure that partially joins the inner layer and the outer layer to each other via multiple gaps penetrating inner and outer surfaces of the reinforcement member. A joint structure that is not fixed to the reinforcement member may be provided such that the reinforcement member may be restrained from being misaligned in the axial direction relative to the balloon. According to the configuration, the reinforcement member is restrained from being misaligned in the axial direction relative to the balloon. Therefore, a state of the balloon reinforced by the reinforcement member can be suitably maintained. The balloon is thus not ruptured while being under low pressure even after repeating inflation and deflation of the balloon multiple times. Therefore, the catheter can be stably used.

The joint structure of the catheter may have multiple fused portions respectively penetrating the multiple gaps of the reinforcement member. The reinforcement member may be movable relative to the fused portions. According to this configuration, the wire member forming the reinforcement member may be caught by the fused portion. Therefore, the reinforcement member is appropriately restrained from being misaligned. It is thus possible to simply realize a structure in which the reinforcement member is effectively restrained from being misaligned in the axial direction, without fixing the reinforcement member to the inner layer and the outer layer through the joint structure.

The joint structure may be provided in only a region of the reinforcement member on the first end portion side and a region of the reinforcement member on the second end portion side. This configuration effectively restrains the reinforcement member from being misaligned in the axial direction while achieving favorable flexibility of the balloon.

The multiple gaps may be meshes in the reinforcement member (i.e., the reinforcement member may be mesh). The meshes in the reinforcement member can be utilized to join the inner layer and the outer layer, and so there is no need to provide a dedicated gap for joining the inner layer and the outer layer to each other.

The reinforcement member of the catheter may include one or more wire members. A lubricant may be present on at least an outer surface of the wire member such that friction between portions of the wire members in contact with each other may be reduced. The lubricant on at least the outer surface of the wire remember can reduce friction between the portions of the wire members in contact with each other, and the degree of freedom of movement between the wire members can be enhanced. Therefore, when being deflated again after inflation, the balloon can easily restore the original shape (thickness) before being inflated.

The lubricant may be applied to the wire member. This allows the amount of lubricant used to be restrained, and friction between the portions of the wire members in contact with each other can be efficiently reduced.

An accommodation chamber accommodating the reinforcement member may be formed between the inner layer and the outer layer of the balloon of the catheter. The accommodation chamber may be filled with the lubricant. Filling the accommodation chamber with the lubricant allows the lubricant to be maintained around the wire member configuring the reinforcement member. Therefore, friction between the portions of the wire members in contact with each other can be reliably reduced.

The wire member of the catheter may be formed of a high-strength fiber possessing a tensile break strength equal to or greater than 2 GPa and an elastic modulus equal to or greater than 50 GPa. Generally, frictional resistance between high-strength fibers (super fibers) is high. Therefore, when the reinforcement member is configured with the high-strength fiber, if the fibers are in direct contact with each other without being lubricated, there is a possibility that when the balloon is deflated again, it may be difficult for the balloon to restore the original shape before being inflated. In contrast, when a lubricant is present on the outer surface of the wire member (string) formed of the high-strength fiber, a problem of frictional resistance occurring when a high-strength fiber is used as the wire member can be restrained (mitigated), and high-pressure resistance and low compliance properties can be effectively applied to the balloon.

In another aspect, the catheter includes an elongated shaft extending in an axial direction and a balloon connected to the shaft. The balloon includes a tubular elastic inner layer and a tubular elastic outer layer. The inner and outer layers are inflatable and deflatable in response to a change of internal pressure of the balloon. The outer layer possesses an inner surface and the inner layer possesses an outer surface. At least a portion of the inner surface of the outer layer is spaced radially outwardly from at least a portion of the outer surface of the inner layer. The catheter includes an accommodation chamber formed by the portion of the inner surface of the outer layer spaced radially outwardly from the portion of the outer surface of the inner layer. The catheter also includes a reinforcement member in the accommodation chamber. The reinforcement member has a first end portion and a second end portion opposite the first end portion in the axial direction. The reinforcement member includes an intermediate portion extending between the first end portion and the second end portion in the axial direction. At least one of the first end portion and the second end portion are movable relative to both the inner layer and the outer layer; and the intermediate portion is movable relative to both the inner layer and the outer layer. Another aspect of the disclosure involves a catheter manufacturing method of manufacturing a catheter sized to be inserted in a living body. The catheter manufacturing method includes positioning a reinforcement member between an inner layer and an outer layer. The inner layer and outer layer are tubular and extend in an axial direction. The inner layer and outer layer are elastic. The inner and outer layers have a first end portion and a second end portion opposite the first end portion in the axial direction. The reinforcement member has a first end portion, a second end portion opposite the first end portion in the axial direction, and an intermediate portion between the first and second end portions of the reinforcement member. The method further includes joining the first end portion of the inner layer to the first end portion of the outer layer while the reinforcement member is positioned between the inner layer and the outer layer in the radial direction, and joining the second end portion of the inner layer to the second end portion of the outer layer while the reinforcement member is positioned between the inner layer and the outer layer in the radial direction. The first end portion of the inner layer is joined to the first end portion of the outer layer and the second end portion of the inner layer is joined to the second end portion of the outer layer without directly fixing the intermediate portion of the reinforcement member to both the inner and outer layers and without directly fixing at least one of the first end portion and the second end portion of the reinforcement member to both the inner layer and the outer layers.

A catheter manufacturing method of manufacturing a catheter is disclosed in this application which includes a balloon that has an inner layer and an outer layer having elastic stretching properties, having tubular shapes, and being able to be inflated and deflated in response to a change of internal pressure, and a reinforcement member that is disposed between the inner layer and the outer layer and has a tubularly net-shaped structure; and in which the reinforcement member has a first end portion and a second end portion in an axial direction, and an intermediate portion configuring a portion between the first end portion and the second end portion. The catheter manufacturing method includes a disposition step of disposing the reinforcement member between the inner layer and the outer layer, and a joint step of joining one end portion of the inner layer and one end portion of the outer layer to each other and the other end portion of the inner layer and the other end portion of the outer layer to each other without directly fixing at least one of the first end portion and the second end portion, and the intermediate portion to the inner layer and the outer layer.

According to the catheter manufacturing method, it is possible to manufacture a catheter which includes a balloon having high flexibility as well as high-pressure resistance and low compliance properties.

The catheter manufacturing method may further include a fusing step of partially fusing the inner layer and the outer layer to each other via a gap penetrating inner and outer surfaces of the reinforcement member without fixing the reinforcement member to the inner layer and the outer layer. Accordingly, there is provided a structure in which the reinforcement member is restrained from being misaligned in the axial direction relative to the inner layer and the outer layer. Therefore, even after repeating inflation and deflation multiple times, the balloon is not ruptured while being under low pressure.

The catheter manufacturing method may further include a step of providing the reinforcement member which is wetted with liquid. In the fusing step, when the reinforcement member wetted with the liquid is disposed between the inner layer and the outer layer, the inner layer and the outer layer may be heated and be fused to each other. Accordingly, the reinforcement member wetted with the liquid is not fused to the inner layer and the outer layer during the fusing step. Thus, it is possible to simply form a structure in which even though the inner layer and the outer layer are partially fused to each other, the reinforcement member is movable relative to the inner layer and the outer layer.

In the catheter manufacturing method, one or more regions in each of the inner layer and the outer layer in the axial direction may be selectively heated in the fusing step. Accordingly, the reinforcement member can be effectively restrained from being misaligned in the axial direction while achieving favorable flexibility of the balloon.

Only a spot of the gap in the reinforcement member may be irradiated with a laser such that the inner layer and the outer layer may be fused to each other in the catheter manufacturing method. Accordingly, the inner layer and the outer layer can be fused to each other at a spot avoiding the wire member without wetting the reinforcement member with liquid.

The entirety of the balloon may also be heated in the fusing step of the catheter manufacturing method. Accordingly, the fusing step can be efficiently carried out.

Flexibility of the balloon reinforced with the reinforcement member can be improved in the catheter and the catheter manufacturing method described here.

BRIEF DESCRIPTION OF THE DRAWINGS

FIG. 3A is a side view illustrating a reinforcement member when inflated, and FIG. 3B is a side view illustrating the reinforcement member when deflated.

FIG. 4A illustrates a base material sleeve being prepared, and FIG. 4B illustrates multiple reinforcement members being prepared from the base material sleeve.

FIG. 7A illustrates the distal end of a shaft and the proximal end of a balloon being joined to each other, and FIG. 7B is a second view illustrating the distal end of the shaft and the proximal end of the balloon being joined to each other.

FIG. 8A illustrates an inner tube and the distal end of the balloon being joined to each other, and FIG. 8B is a second view illustrating the inner tube and the distal end of the balloon being joined to each other.

FIG. 9A illustrates a distal tip and the inner tube being joined to each other, and FIG. 9B is a second view illustrating the distal tip and the inner tube being joined to each other.

DETAILED DESCRIPTION

Figure 1:
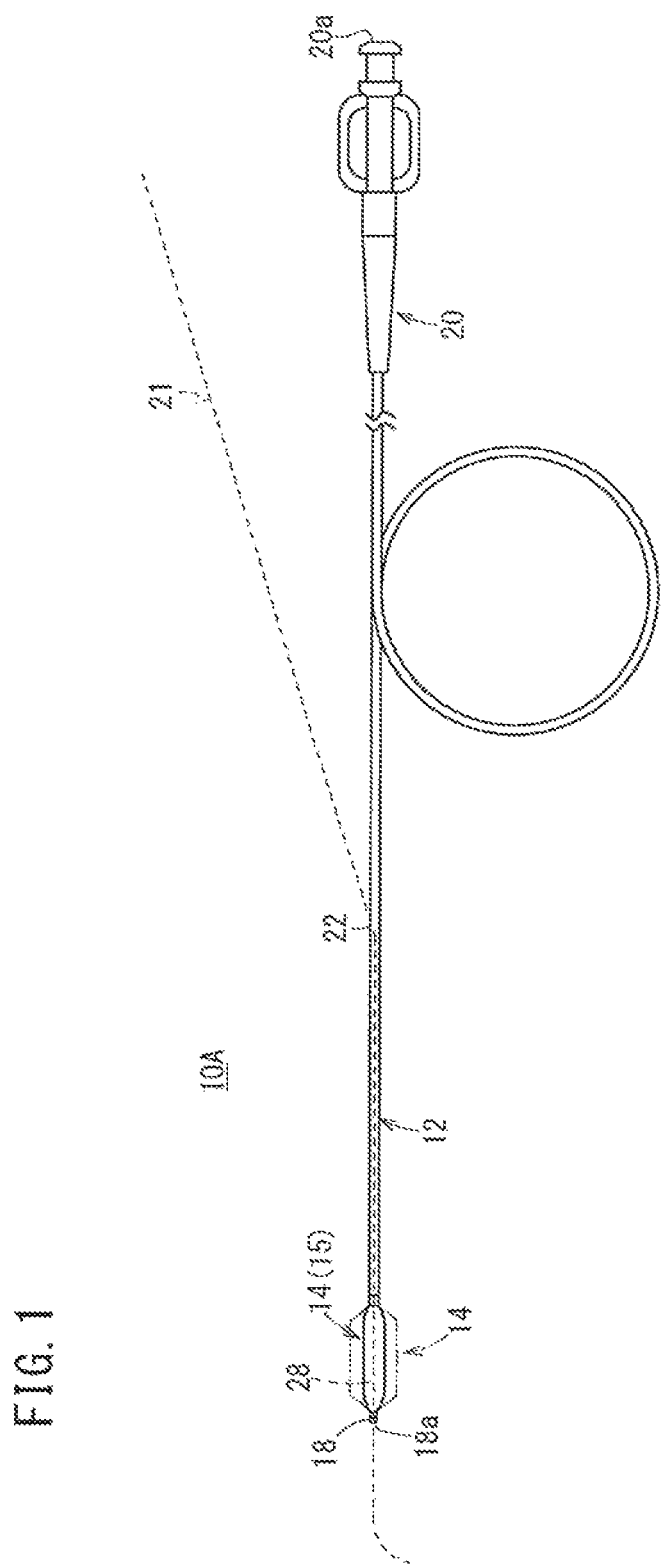
FIG. 1 is a partially-omitted schematic view illustrating a first embodiment of a catheter disclosed here.

Set forth below with reference to the accompanying drawings is a detailed description of embodiments of a catheter and a method for manufacturing a catheter representing examples of the inventive catheter and method disclosed here. In the discussion regarding second and third embodiments and modification examples, the same reference signs (reference numerals) are used in reference to elements which are the same as or similar to those of a first embodiment, and detailed description of such features will not be repeated.

First Embodiment

FIG. 1 is a partially-omitted schematic view illustrating a configuration of a catheter 10A according to the first embodiment. The catheter 10A is a so-called PTCA (percutaneous transluminal coronary angioplasty: percutaneous coronary intervention) inflation catheter for performing treatment in a living body. The catheter 10A includes a long shaft 12 which is inserted through a biological organ (for example, the coronary artery) and a balloon 14 on the distal side of the long shaft 12 is inflated at a stenosed portion (lesion). The stenosed portion is thereby widened.

The aspects of the catheter described here can also be applied to a catheter other than a PTCA inflation catheter. For example, the catheter can be for improving a lesion formed inside biological organs such as other blood vessels, the bile duct, the trachea, the esophagus, the urethra, and other internal organs.

Figure 2:
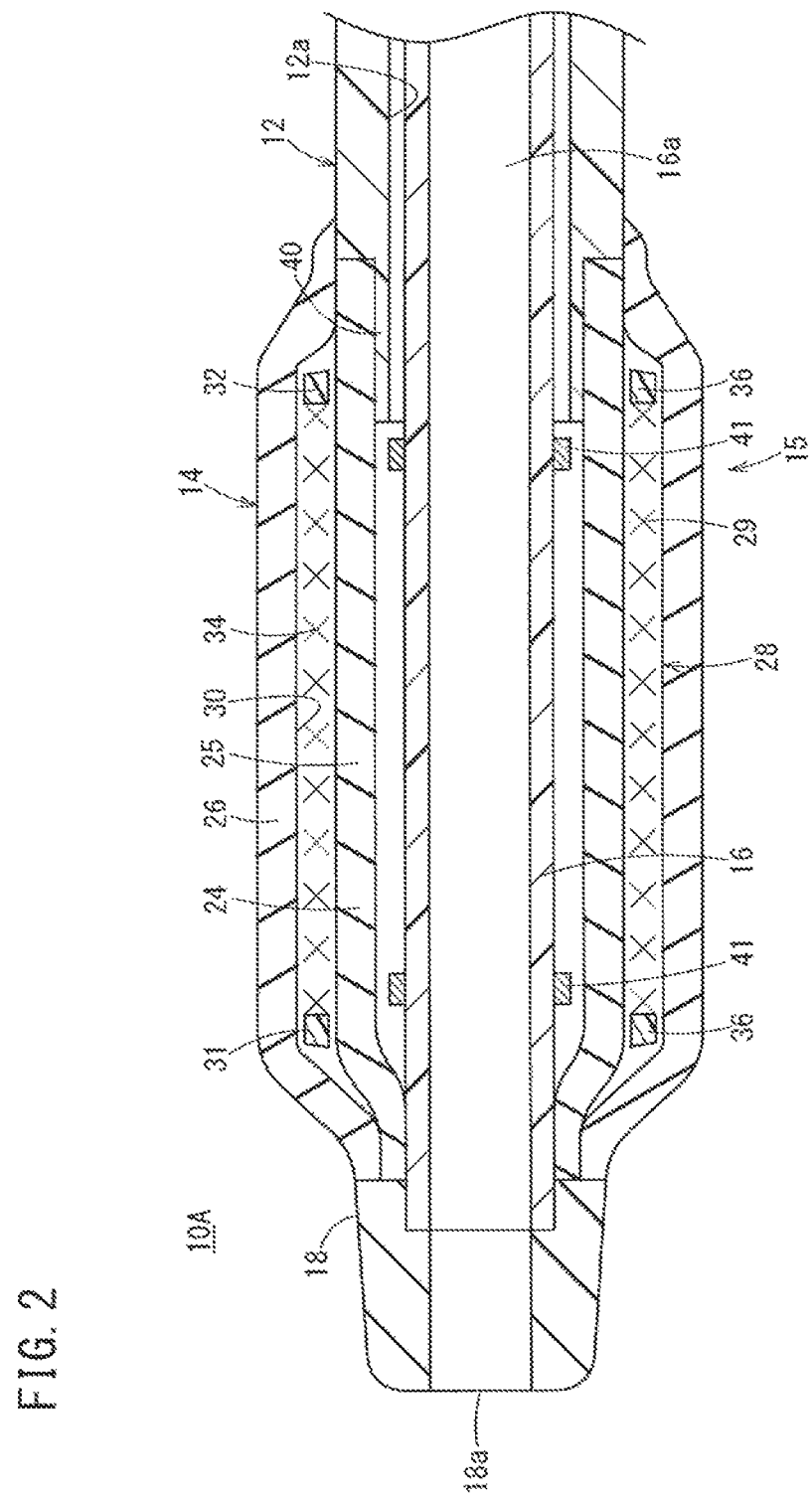
FIG. 2 is a schematic cross-sectional view of the distal portion of the catheter illustrated in FIG. 1.

As illustrated in FIGS. 1 and 2, the catheter 10A includes the long shaft 12 possessing a small diameter, the balloon 14 joined to the distal end of the shaft 12, a reinforcement member 28 disposed inside a membrane (wall) configuring the balloon 14, an inner tube 16 inserted through the shaft 12 and the balloon 14, a distal tip 18 joined to the distal end of the balloon 14, and a hub 20 on the proximal side of the shaft 12.

The catheter 10A illustrated in FIG. 1 is a so-called "rapid exchange-type" catheter provided with an opening portion 22 through which a guide wire 21 is guided (i.e., through a middle portion of the shaft 12 in a longitudinal direction). In another embodiment, the catheter 10A may be an "over-the-wire-type" catheter in which a guide wire lumen is formed throughout the overall length of the catheter 10A, and the guide wire 21 is guided through the proximal end of the hub 20.

The shaft 12 is a flexible tube with two open ends (i.e., both ends in an axial direction are open). The shaft 12 is relatively long and has a relatively small outer diameter. The shaft 12 extends from the rear end of the balloon 14 to the distal end of the hub 20. A portion from the distal end to the opening portion 22 is a double tube which forms an inflation lumen 12a between the shaft 12 and the inner tube 16. A portion between the opening portion 22 and the hub 20 is a single tube. Inflation fluid for the balloon 14 is supplied through the inflation lumen 12a formed in the shaft 12.

In the shaft 12, the inflation fluid can be fed under pressure to the balloon 14 from a pressure applying apparatus such as an indeflator connected via a luer taper 20a or the like provided in the hub 20. For example, the inflation fluid may be a contrast agent, a physiological salt solution, or a mixture of these fluids.

The inner tube 16 is a guide wire tube forming a wire lumen 16a through which the guide wire 21 is inserted. The distal end of the inner tube 16 is positioned on the distal side beyond the proximal end of the distal tip 18 (i.e., the distal-most end of the inner tube 16 is distal to the proximal-most end of the distal tip 18). The inner tube 16 extends inside the balloon 14 and the shaft 12. The proximal end of the inner tube 16 is liquid-tightly joined to the opening portion 22 (refer to FIG. 1). The opening portion 22 is formed in an intermediate portion of the shaft 12. Therefore, the guide wire 21 can be inserted through a distal end opening portion 18a serving as an entrance at the distal tip 18, through the wire lumen 16a of the inner tube 16 from the distal side toward the proximal side and out through the opening portion 22 serving as an exit.

It is favorable to provide a radiopaque marker 41 in the inner tube 16 inside the balloon 14. The radiopaque marker 41 is configured with an X-ray opaque (radiopaque) material (for example, gold, platinum, tungsten, or a mixture of these metals). The radiopaque marker 41 is used for visually recognizing the position of the balloon 14 in a living body under an X-ray contrast condition. The radiopaque marker 41 can be configured, for example, to have a tubular shape (ring shape). As illustrated in FIG. 2, multiple imaging markers 41 may be provided on the outer surface of the inner tube 16 inside the balloon 14 while being spaced apart from each other in the axial direction. In another embodiment, only one radiopaque marker 41 may be provided on the inner tube 16 inside the balloon 14.

It is preferable that the shaft 12 and the inner tube 16 have structures with appropriate flexibility and appropriate rigidity such that an operator can smoothly insert the long catheter 10A into a biological organ (such as a blood vessel) while grasping and operating the proximal side of the catheter 10A. For example, it may thus be favorable that the shaft 12 and the inner tube 16 are formed of a polymeric material such as polyolefin (for example, polyethylene, polypropylene, polybutene, an ethylene-propylene copolymer, an ethylene-vinyl acetate copolymer, ionomer, and a mixture of two or more types of these materials), polyvinyl chloride, polyamide, a polyamide elastomer, polyurethane, a polyurethane elastomer, polyimide, a fluorine resin, and a mixture thereof; or a multi-layer tube including two or more types of these materials.

The balloon 14 can be inflated and dilated in response to a change of internal pressure (i.e., the balloon 14 is configured to inflate/expand and to deflate/contract). The distal portion of the balloon 14 is joined to a portion in the vicinity of the distal portion of the inner tube 16, and the proximal portion of the balloon 14 is joined to the distal portion of the shaft 12 (e.g., the outer surface of the distal portion of the shaft 12 as shown in FIG. 2). The internal space of the balloon 14 communicates with the inflation lumen 12a.

The inflation fluid can flow into (be guided into) the balloon 14 via the inflation lumen 12a. The inflation fluid can also be discharged from the balloon 14 via the inflation lumen 12a. The balloon 14 inflates when the inflation fluid is guided into the balloon 14. As indicated by the imaginary line in FIG. 1, a portion between the distal end and the proximal end of the balloon exhibits a shape which is increased in diameter and has a substantially uniform outer diameter along the axial direction when the balloon 14 is maximally inflated.

The balloon 14 is required to have appropriate flexibility to pass through a meandering or bent point of a body lumen. The balloon 14 is also required to have strength to the extent that a lesion can be reliably widened and needs to have high-pressure resistance and low compliance properties (i.e., the balloon 14 inflates or expands to an intended outer diameter/shape and does not inflate or expand beyond the intended outer diameter/shape). The balloon 14 illustrated in FIG. 2 has an inner layer 24 and an outer layer 26 having tubular shapes, having elastic stretching properties, and configuring fluid-impermeable balloon walls. The reinforcement member 28 is disposed between the inner layer 24 and the outer layer 26 (i.e., between the inner and outer layers 24, 26 in the radial direction). The balloon 14 and the reinforcement member 28 configure a dilation portion 15 (inflation portion) which can be inflated and deflated in a radial direction at the distal portion of the catheter 10A.

The inner layer 24 transfers force to the reinforcement member 28 in response to the inflation fluid being guided into the balloon 14 (pressurization). The inner layer 24 expands to the extent of a shape which is restricted along the dilated shape of the reinforcement member 28. The outer layer 26 swells (expands) along the inflated shape of the reinforcement member 28 in response to the inflation fluid guided into the balloon 14 (pressurization). The outer layer 26 contracts to the initial shape (i.e., the pre-pressurized shape) in response to the inflation fluid being discharged from the inside of the balloon 14 (decompression), which restores the original shape (position) of the reinforcement member 28. Therefore, it is preferable that the outer layer 26 is formed of a material having a high stretching recovery rate.

The inner layer 24 and the outer layer 26 are joined to each other at the distal portions and the proximal portions of each of the respective inner layer 24 and outer layer 26, for example, through fusing or bonding. An annularly sealed accommodation chamber 30 is formed between the inner layer 24 and the outer layer 26. The accommodation chamber 30 is a chamber between the outer surface of the inner layer 24 and the inner surface of the outer layer 26 in the radial direction that accommodates the reinforcement member 28.

Examples of the inner layer 24 and the outer layer 26 materials include various types of rubber material such as natural rubber, butyl rubber, isoprene rubber, butadiene rubber, styrene-butadiene rubber, and silicone rubber; various types of thermoplastic elastomer such as a polyurethane-based elastomer, a polyester-based elastomer, a polyamide-based elastomer, an olefin-based elastomer, and a styrene-based elastomer; mixtures of these materials; and the like. The material of the inner layer 24 and the material of the outer layer 26 may be the same as each other or may be different from each other.

The reinforcement member 28 is a tubularly net-shaped (e.g., mesh) member. The reinforcement member 28 is positioned as an intermediate layer between the inner layer 24 and the outer layer 26, and the reinforcement member 28 functions to enhance pressure resistance of the balloon 14. The reinforcement member 28 is formed to have the tubularly net-shaped body by knitting (weaving) one or more threads 29 into the tubular net shape. The reinforcement member 28 has stretching properties in at least a circumferential direction (and the radial direction) (i.e., the reinforcement member 28 can stretch/expand outward in the circumferential or radial directions). The method of forming the reinforcement member 28 is not limited to any particular form. Examples of the method to form the reinforcement member 28 include tube-knitting and braiding. In a case of tube-knitting, the threads 29 are extended in the circumferential direction in a waved (wavy or wave-shaped) manner and are arranged in the axial direction, and the waved threads 29 adjacent to each other in the axial direction are interlaced with each other (refer to FIG. 3A) to form the reinforcement member 28. In a case of braiding, one or more threads 29 extending in a first spiral direction and one or more threads 29 extending in a second spiral direction are woven so as to intersect each other, thereby forming the tubularly net-shaped body.

In order to impart high-pressure resistance and low compliance properties to the balloon 14 (i.e., the balloon 14 inflates to an intended outer diameter/shape), it is preferable to employ a thread 29 having high strength and a high elastic modulus. For example, it is preferable to utilize a twisted thread formed of high-strength fibers (super fibers) possessing a tensile break strength equal to or greater than 2 GPa and an elastic modulus equal to or greater than 50 GPa. Examples of the high-strength fiber include an aramid fiber, a carbon fiber, a polyarylate fiber, a PBO fiber, ultra-high molecular weight polyethylene, and an LCP fiber.

For example, the outer diameter of the thread 29 may range approximately from 5 to 100 μm. When the twisted thread formed of high-strength fibers is used as the thread 29, for example, a single fiber outer diameter of the high-strength fiber may range approximately from 5 to 30 μm. For example, a single fiber outer diameter of 12 μm can be used for the high strength fiber. However, a thinner fiber may be used or a thicker fiber may be used. When using a thicker fiber, it is favorable to employ a loosely twisted thread that is in an unraveled state when tensile force is not applied to the twisted thread.

The reinforcement member 28 includes two end portions (first end portion 31 and second end portion 32) opposite one another in the axial direction and an intermediate portion 34 between the first end portion 31 and the second end portion 32. The intermediate portion 34 is not directly fixed to the inner layer 24 and the outer layer 26 and at least one of the first end portion 31 and the second end portion 32 is not directly fixed to the inner layer 24 and the outer layer 26. Accordingly, movement of the reinforcement member 28 relative to the inner layer 24 and the outer layer 26 in the axial direction and the circumferential direction is allowed.

In addition, the inner layer 24 and the outer layer 26 may be fixedly attached (for example, fused or bonded) via a gap (mesh) between the threads 29 forming the reinforcement member 28. Accordingly, while the reinforcement member 28 is allowed to move relative to the inner layer 24 and the outer layer 26 to a certain extent in the axial and/or radial directions, the moving range of the reinforcement member 28 can be restricted.

In the embodiment illustrated in FIG. 2, the other one of the first end portion 31 and the second end portion 32 is also not directly fixed to the inner layer 24 and the outer layer 26 (i.e., both the first end portion 31 and the second end portion 32 are not directly fixed to the inner layer 24 and the outer layer 26 in the FIG. 2 embodiment). Accordingly, the reinforcement member is allowed to move relative to the inner layer 24 and the outer layer 26 in the axial direction. In other words, the reinforcement member 28 is not fixed to any one of the inner layer 24 and the outer layer 26 in the present embodiment. Therefore, the reinforcement member 28 can freely move in the circumferential direction and the axial direction within the accommodation chamber 30 between the outer surface of the inner layer 24 and the inner surface of the outer layer 26 (within the range restricted between the inner layer 24 and the outer layer 26).

Only one of the first end portion 31 and the second end portion 32 may be fixed to the inner layer 24 or the outer layer 26 (i.e., at least one of the first end portion 31 and the second end portion 32 is not fixed to the inner layer 24 or to the outer layer 26). The fixing means to fix the end portion (i.e., either the first end portion 31 or the second end portion 32) to the inner layer 24 and outer layer 26 is not limited to any particular means and suitable fixing means such as fusing and bonding may be employed.

Inflation of the first end portion 31 and the second end portion 32 of the reinforcement member 28 in the circumferential direction and the radial direction is restricted by an inflation restriction portion 36. The inflation restriction portion 36 is not limited to a particular configuration. Examples of the inflation restriction portion 36 include configurations such as a knitted portion in which inflation of the inflation restriction portion 36 in the circumferential direction and the radial direction is restricted through a knitting method, ring-shaped fused portions which are formed at the first end portion 31 and the second end portion 32 by fusing threads (fibers) having fusing properties (i.e., are compatible for fusing) to each other, and ring-shaped retention members which are respectively fixed to the first end portion 31 and the second end portion 32.

As illustrated in FIG. 2, the distal portion of the inner layer 24 is joined to the outer surface of the inner tube 16. The proximal portion of the inner layer 24 is joined to the outer surface of the distal portion (thin portion 40) of the shaft 12. The outermost distal portion of the thin portion 40 of the shaft 12 is positioned distally beyond the innermost proximal surface of the inner layer 24, on the inner side of the inner layer 24 (the outer surface of the thin portion 40 faces the inner surface of the inner layer 24 at a proximal portion of the inner layer 24). Therefore, a region (hereinafter, will be referred to as "stretchable region 25 of the inner layer 24") in the inner layer 24 that is stretchable during deformation of inflation and deflation of the balloon 14 is between a joint spot (i.e., the joining location) of the inner layer 24 and the inner tube 16, and the outermost distal portion of the thin portion 40 of the shaft 12.

The innermost proximal portion (i.e., the proximal-most end) of the reinforcement member 28 is positioned proximally beyond the innermost proximal portion (i.e., the proximal-most end) of the stretchable region 25 in the inner layer 24. As illustrated in FIG. 2, the second end portion 32 of the reinforcement member 28 may be positioned proximally beyond the distal-most end of the thin portion 40 of the shaft 12 in the accommodation chamber 30 formed between the inner layer 24 and the outer layer 26 of the balloon 14. Accordingly, when the balloon 14 is inflated, the second end portion 32 of the reinforcement member 28 is less affected by inflation of the balloon 14 and contributes to the restriction of the maximally inflated diameter of the balloon 14 performed by the reinforcement member 28.

FIG. 3A is a side view illustrating the reinforcement member 28 when inflated, and FIG. 3B is a side view illustrating the reinforcement member 28 when deflated. As illustrated in FIG. 3A, when the reinforcement member 28 is inflated in the circumferential direction, the threads 29 are in a tensed state, and the outer diameter of the reinforcement member 28 is not increased beyond a certain extent (i.e., the outer diameter of the reinforcement member 28 does not increase beyond a predetermined outer diameter when being inflated). Since inflation of the first end portion 31 and the second end portion 32 is restricted, the shape of the reinforcement member 28 (intermediate portion 34) when being inflated includes a straight portion 42 having a substantially uniform outer diameter and outer-diameter varying portions (tapered portions) 45 and 46 which are respectively positioned on both sides of the straight portion 42 in the axial direction and decrease in outer diameter from the straight portion 42 to the respective end portion (i.e., the first end portion 31 or the second end portion 32) in the axial direction.

When the balloon 14 contains the reinforcement member 28 illustrated in FIGS. 3A and 3B, the balloon 14 includes a straight portion having a substantially uniform outer diameter due to the reinforcement member 28 and outer-diameter varying portions (tapered portions) which are respectively positioned on both sides of the straight portion and are decreased in outer diameter in the axial direction when the balloon 14 is inflated. The radiopaque marker 41 is disposed on the inner tube 16 such that the position of the straight portion of the balloon 14 can be confirmed. Accordingly, positioning the region of the maximally dilated diameter in the balloon 14 relative to the lesion can be easily performed because an operator can visually recognize the position having the maximally inflated diameter in the balloon 14 under an X-ray contrast condition.

When the reinforcement member 28 is formed through the knitting method in which the waved threads 29 adjacent to each other in the axial direction are interlaced with each other, the threads 29 are folded and the reinforcement member 28 is decreased in outer diameter when the reinforcement member 28 is compressed in the circumferential direction as illustrated in FIG. 3B. When the reinforcement member 28 is compressed in the axial direction, the threads 29 of the meshes become misaligned and the threads 29 adjacent to each other in the axial direction can overlap each other. Moreover, the reinforcement member 28 can be bent in accordance with rotations of the interlaced portion between the threads 29 adjacent to each other in the axial direction. Therefore, the reinforcement member 28 has excellent flexibility with respect to bending.

In FIGS. 1 and 2, the distal tip 18 provided on the distal side of the balloon 14 is a distal-most portion of the catheter 10A which flexibly advances through a curved portion, an irregular portion, and the like inside a biological organ, penetrates a lesion (stenosed portion), and leads the catheter 10A to be smoothly inserted through the lesion. The distal tip

18 is a short tube having an inner diameter substantially the same as the inner diameter of the inner tube 16.

The distal tip 18 is fitted to the distal portion of the inner tube 16 from the outside so as to be liquid-tightly joined to the distal portion of the inner tube 16 (the distal tip 18 is fixed to the outer surface and distal-most face of the inner tube 16 as illustrated in FIG. 2). The distal tip 18 protrudes toward the distal side beyond the opening portion of the wire lumen 16a. The proximal surface of the distal tip 14 (i.e., the surface at the proximal-most end of the distal tip 14) is joined to the distal surface of the balloon 14. The distal end opening portion 18a of the distal tip 18 communicates with the wire lumen 16a of the inner tube 16 and serves as the entrance of the guide wire 21.

The material and the shape of the distal tip 18 are suitably selected such that the distal tip 18 is configured to be more flexible than at least the shaft 12 and the inner tube 16. Note that, the distal tip 18 may be omitted in some embodiments. When the distal tip 18 is omitted, it is favorable to employ a configuration in which the outermost distal end position of the inner tube 16 and the outermost distal end position of the balloon 14 coincide with each other, or a configuration in which the outermost distal end position of the inner tube 16 slightly protrudes beyond the outermost distal end position of the balloon 14.

An example of a method of manufacturing the catheter 10A (mainly, a step of manufacturing the dilation portion 15 and peripheral portions of the dilation portion 15) will now be described. Note that, the disclosed method of manufacturing the catheter 10A is not limited to any exemplified manufacturing method described here. In FIGS. 4A to 9B, the tubularly net-shaped reinforcement member 28 is schematically illustrated, and the reinforcement member 28 is not limited to any particular knitting method.

FIGS. 4A and 4B are views illustrating steps of manufacturing the reinforcement member 28. First, a step of preparing a tubularly net-shaped base material sleeve 50 which becomes the base material of the reinforcement member 28 (step of preparing a base material sleeve) is executed as illustrated in FIG. 4A. The base material sleeve 50 has a length equal to or greater than those of multiple reinforcement members 28. As illustrated in FIG. 4A, for example, the base material sleeve 50 is formed by knitting the above-described high-strength fibers to have a tubular net shape.

As illustrated in FIG. 4B, the base material sleeve 50 is then cut at one or more spots in the axial direction to become multiple divided sleeves 51 and the above-described inflation restriction portion 36 (cutting and restriction processing step) is subsequently formed at both end portions of each divided sleeve 51. Accordingly, multiple reinforcement members 28 are obtained.

Figure 5A:
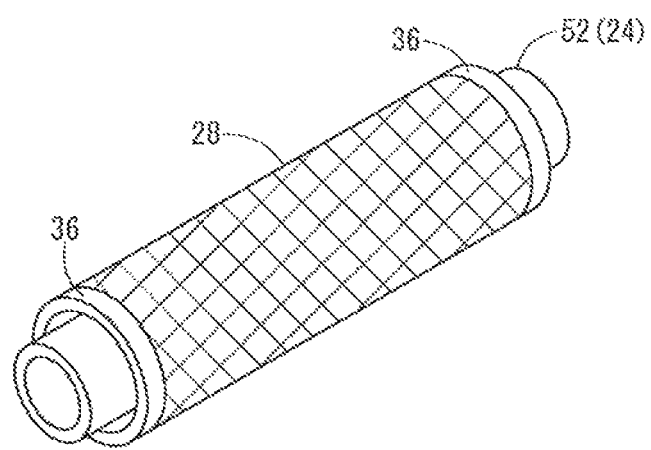
FIG. 5A illustrates an inner layer tube being covered with the reinforcement member.

Subsequently, the inner layer tube 52, which is the base material of the inner layer 24, is covered by the reinforcement member 28 (first covering step) as illustrated in FIG. 5A. Both end portions of the inner layer tube 52 may respectively protrude beyond openings at both ends of the reinforcement member 28 as shown in FIG. 5A.

Figure 5B:
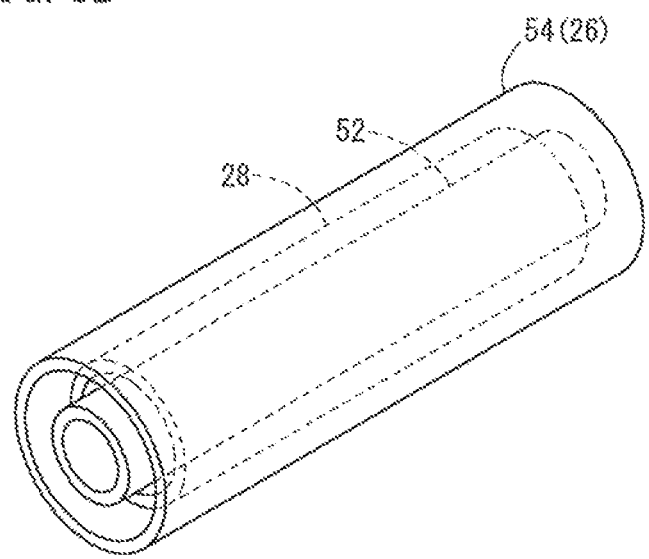
FIG. 5B illustrates the inner layer tube and the reinforcement member being covered with an outer layer tube.

The inner layer tube 52 and the reinforcement member 28 (i.e., the reinforcement member 28 in a state where the inner layer tube 52 is inserted within the interior of the reinforcement member 28) are then covered by an outer layer tube 54 (second covering step). The outer layer tube 54 is the base material of the outer layer 26. As shown in FIG. 5B, the inner layer tube 52 and the reinforcement member 28 are covered by the outer layer tube 54 such that the overall length of the reinforcement member 28 is housed inside the outer layer tube 54 (both end portions of the outer layer 26 protrude in the axial direction beyond both of the end portions of the reinforcement member 28).

Figure 6A:
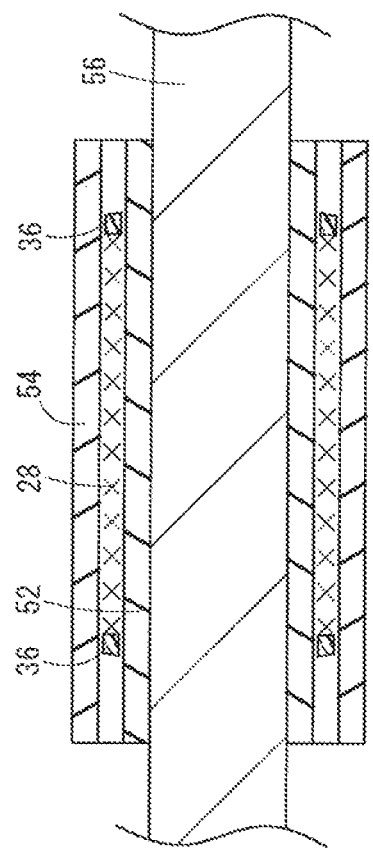
FIG. 6A illustrates the inner layer tube and the outer layer tube being joined to each other.
Figure 6B:
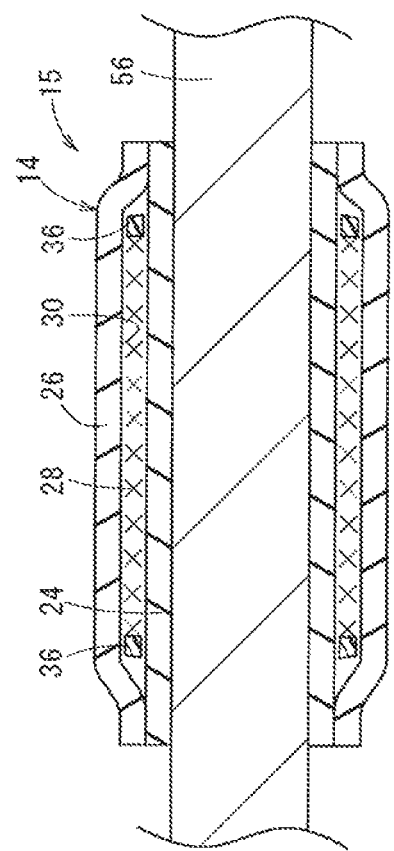
FIG. 6B is a second view illustrating the inner layer tube and the outer layer tube being joined to each other.

A step of joining the inner layer tube 52 and the outer layer tube 54 (step of joining inner and outer layers) is next executed. As illustrated in FIG. 6A, a mandrel 56 (core bar) is inserted into the inner layer tube 52 (i.e., into the interior of the assembly of the inner layer tube 52, the outer layer tube 54, and the reinforcement member 28). One end portion of the inner layer tube 52 and one end portion of the outer layer tube 54 are then fused to be joined to each other, and the other end portion of the inner layer tube 52 and the other end portion of the outer layer tube 54 are fused to be joined to each other. Accordingly, the annularly sealed accommodation chamber 30 is created between the inner layer 24 and the outer layer 26, thereby obtaining the inflation portion 15 in a state where the reinforcement member 28 is located inside the accommodation chamber 30. After the step of joining inner and outer layers, the mandrel 56 is removed.

In the present embodiment, the reinforcement member 28 is merely disposed inside the accommodation chamber 30 and is not joined to other members through fusing, bonding, or the like. Therefore, the reinforcement member 28 is not fixed to any portion of the balloon 14 (i.e., to the inner layer 24 and outer layer 26).

Subsequently, a step of joining the balloon 14 (inflation portion 15) and the shaft 12 to each other (step of joining a balloon and a shaft) is executed as illustrated in FIGS. 7A and 7B. The thin portion 40 is first formed at the distal portion of the shaft 12. To form the thin portion 40, for example, the distal portion of the shaft 12 is drawn down (the mandrel is inserted into a hollow portion of the shaft 12, and the distal portion of the shaft 12 is pressedly input into a mold which includes a hole having a diameter smaller than that of the shaft 12). Therefore, the distal portion can have a small outer diameter (i.e., smaller than the outer diameter of the rest of the shaft 12). The thin portion 40 of the shaft 12 is inserted into the interior of the proximal side of the balloon 14 as shown in FIG. 7A. Subsequently, as illustrated in FIG. 7B, the proximal portion of the balloon 14 and the distal portion (thin portion 40) of the shaft 12 are fused to be joined to each other.

The radiopaque marker 41 is attached to the outer surface of the inner tube 16 (the attached radiopaque marker 41 is shown in FIG. 8A). Specifically, the tubular radiopaque marker 41 having an inner diameter slightly greater than the inner tube 16 is moved around the outer side of the inner tube 16, and the mandrel is inserted into the inner tube 16. Thereafter, the entire circumference of the radiopaque marker 41 is beaten (swaging step). The inner diameter of the radiopaque marker 41 is thus decreased to contact/ engage with the outer surface of the inner tube 16. In this manner, the imaging marker 41 is fixed to the inner tube 16.

The balloon 14 and the inner tube 16 are then joined to each other (step of joining a balloon and an inner tube) as shown in FIGS. 8A and 8B. The inner tube 16 is first inserted into the interior of the balloon 14 and the shaft 12 as illustrated in FIG. 8A. The distal portion of the balloon 14 and the inner tube 16 are then fused to be joined to each other as shown in FIG. 8B.

Subsequently, a step of joining the distal tip 18 and the inner tube 16 to each other (step of joining a distal tip and an inner tube) is executed as shown in FIGS. 9A and 9B. First, the distal portion of the inner tube 16 is cut, thereby adjusting the length as shown in FIG. 9A. The proximal portion of the distal tip 18 is fitted to the distal portion of the inner tube 16 from the outside, and the proximal portion of the distal tip 18 and the distal portion of the inner tube 16 are fused to be joined to each other as illustrated in FIG. 9B.

Note that, joining the proximal end of the shaft 12 and the distal portion of the hub 20 to each other (step of joining a shaft and a hub) can be executed at an arbitrary time. For example, the step of joining a shaft and a hub may be executed before the step of joining the balloon 14 and the shaft 12, may be executed after the step of joining the distal tip 18 and the inner tube 16, or may be executed between the step of joining the balloon 14 and the shaft 12 and the step of joining the distal tip 18 and the inner tube 16.

In the above-described manufacturing method, fusing is described as an example for a method of joining members to one another. However, other types of joint means such as bonding may instead be applied.

The catheter 10A according to the present embodiment is basically configured as described above. Operations and effects of the catheter 10A will now be described.

An example of performing treatment using the catheter 10A is as follows. First, a lesion (stenosed portion) occurring inside a blood vessel is specified (identified) through an intravascular contrast method or an intravascular ultrasound diagnosis method. A guide wire 21 is percutaneously guided into the blood vessel in advance through, for example, Seldinger's method. The guide wire 21 is then inserted through the wire lumen 16a of the inner tube 16 from the distal end opening portion 18a of the distal tip 18. While the guide wire 21 is guided out through the opening portion 22, the catheter 10A is inserted into the blood vessel. Under a radioscopic condition, the guide wire 21 is caused to advance toward the target lesion. The guide wire 21 is moved to pass through the lesion and to indwell, and the catheter 10A is moved to advance along the guide wire 21.

When the distal tip 18 of the catheter 10A passes through the lesion, the balloon 14 is positioned at the lesion. Inflation fluid (for example, contrast agent) is then pressure-fed into the dilation lumen 12a from the hub 20 side to inflate the balloon 14 and widen the lesion. Accordingly, treatment of the lesion can be performed. Subsequently, the inflation fluid is suctioned from the inside of the balloon 14 to the hub 20 side through the inflation lumen 12a, and the balloon 14 is deflated again. When an additional lesion required to be treated is present at a different spot inside a body lumen, the balloon 14 is delivered (maneuvered) to the additional lesion and inflated and deflated in a similar manner as described above to widen the additional lesion. When the procedure for all of the lesion areas in a treatment object is completed, the catheter 10A is removed from the body.

As described above, in the reinforcement member 28 of the catheter 10A according to the present embodiment, at least one of the first end portion 31 and the second end portion 32, and the intermediate portion 34 are not fixed to the balloon 14. Here, the expression "at least one of the first end portion 31 and the second end portion 32, and the intermediate portion 34 are not directly fixed to the inner layer 24 and the outer layer 26" denotes that at least one of the first end portion 31 and the second end portion 32 is not bonded to the inner layer 24 and the outer layer 26 and is not embedded in the inner layer 24 and the outer layer 26, and the intermediate portion 34 is not bonded to the inner layer 24 and the outer layer 26 and is not embedded in the inner layer 24 and the outer layer 26, thereby allowing the reinforcement member 28 to freely move inside the accommodating chamber 30 formed between the inner layer 24 and the outer layer 26. In other words, substantially the entirety of the reinforcement member 28 has a degree of freedom for moving in the axial direction and the circumferential direction relative to the balloon 14. Favorable flexibility of the balloon 14 can thus be maintained. Accordingly, it is possible to realize the balloon 14 having high passing properties (i.e., maneuverability) inside a body lumen.

In the embodiment illustrated in FIG. 2, not only one of the first end portion 31 and the second end portion 32 but also the other of the first and second end portions 31, 32 is not fixed to any one of the inner layer 24 and the outer layer 26. The reinforcement member 28 is thus not fixed to any location of the balloon 14. Therefore, the degree of freedom for moving the reinforcement member 28 relative to the balloon 14 can be further improved and flexibility can be improved. This configuration also allows for improved crossability (maneuverability) inside a body lumen.

The reinforcement member 28 is positioned between the inner layer 24 and the outer layer 26 which each have elastic stretching properties (i.e., the inner and outer layers 24, 26 are relatively elastic/flexible). Therefore, high-pressure resistance and low compliance properties can be suitably applied to the balloon 14.

Figure 10:
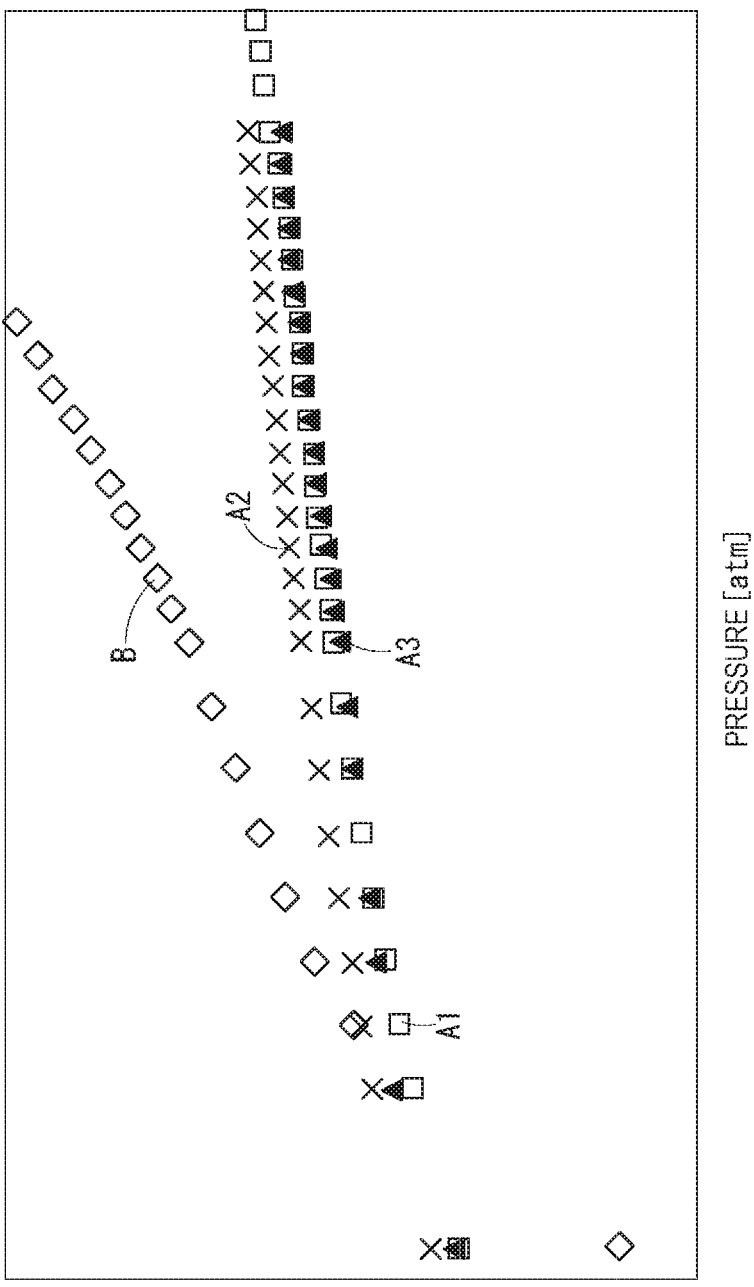
FIG. 10 is a graph illustrating the relationship between pressure and balloon outer diameter regarding balloons having different forms of fixing the reinforcement member from each other, and a balloon without a reinforcement member.

FIG. 10 is a graph illustrating the relationship between pressure and balloon outer diameter regarding balloons A1 to A3. Balloons A1 to A3 are provided with the reinforcement member 28, but have different forms of fixing the reinforcement member 28. Balloon B is not provided with a reinforcement member 28. The balloon A1 has both end portions of the reinforcement member 28 in the axial direction fixed to the inner layer 24, the balloon A2 has only one end portion of the reinforcement member 28 in the axial direction fixed to the inner layer 24, and the balloon A3 has the reinforcement member 28 not fixed to any location of the inner layer 24.

As illustrated in FIG. 10, the balloons A1 to A3 provided with the reinforcement member 28, compared to the balloon B provided without a reinforcement member 28, have gentle (i.e., relatively smaller) increases of balloon outer diameters relative to increases in internal pressure. Balloons A1 to A3 possess high pressure resistance and low compliance properties relative to balloon B that does not include the reinforcement member 28. Meanwhile, no meaningful (significant) difference based on the type of fixing the reinforcement member 28 is recognized in the balloons A1 to A3 that are provided with the reinforcement member 28. Therefore, it is understood that a balloon having high-pressure resistance and low compliance properties can be realized by providing the reinforcement member 28 between the inner layer 24 and the outer layer 26, regardless of whether the reinforcement member 28 is fixed. From the viewpoint of maintaining favorable flexibility of the balloon 14 and improving crossability of the catheter 10A inside a body lumen, it is thus favorable that the intermediate portion 34 and at least one the end portions of the reinforcement member 28 are not fixed to the inner layer 24 and the outer layer 26 of the balloon 14.

In addition, the balloon 14 of the present embodiment is inflated and deflated while entailing elastic stretching and is a zero folding-type balloon (which is not folded when being in a deflated state). Accordingly, the balloon can easily restore the original outer diameter when the balloon is deflated. When multiple lesions occur in different locations inside a body lumen, the same balloon 14 can be used to treat the multiple lesions because the outer diameter of the balloon 14 after being deflated does not become greater than the initial outer diameter of the balloon 14. Therefore, even after the balloon 14 is deflated again, favorable crossability (maneuverability) inside a body lumen can be maintained.

The balloon 14 having elastic stretching properties (i.e., a relatively elastic balloon 14) can be prepared without performing blow molding. Therefore, the catheter 10A can be conveniently manufactured. In other words, when a balloon is configured with a non-stretchable material, the balloon is required to be molded to have a desired shape by executing blow molding after manufacturing the base material of the balloon. Moreover, there is a need to execute a wrapping step in which the balloon is folded (one or more outer circumferential portions of the balloon are folded in the circumferential direction in an overlapping manner) to put the balloon in a deflated state. In contrast, the balloon 14 of the present embodiment does not require blow molding and does not require the wrapping step during manufacturing. Therefore, it is possible to reduce the number of manufacturing steps and to lower the manufacturing cost.

In addition, inflation in the circumferential direction and the radial direction is restricted by the inflation restriction portion 36 (refer to FIG. 2) at the first end portion 31 and the second end portion 32 of the reinforcement member 28. According to this configuration, the maximally inflated diameter of the intermediate portion 34 of the reinforcement member 28 positioned between the first end portion 31 and the second end portion 32 can be effectively restricted. Therefore, the function as the reinforcement member 28 can be suitably conducted.

As described above, the reinforcement member 28 may be formed by tubularly knitting one or more threads 29, and the waved threads 29 adjacent to each other in the axial direction are interlaced (refer to FIG. 3A). When the reinforcement member 28 is compressed in the circumferential direction, the threads 29 become folded in the circumferential direction. When the reinforcement member 28 is compressed in the axial direction, the threads 29 of the meshes become misaligned in the axial direction. Therefore, the reinforcement member 28 in this configuration can be flexibly bent.

In the reinforcement member 28 in which the meandering (i.e., wavy or bent) threads 29 adjacent to each other in the axial direction are interlaced with each other, the interlaced portion of the threads 29 configures an interlock portion. In the interlock portion, the threads 29 are not bonded to each other. The threads 29 are formed to be movable relative to each other. According to this configuration, the reinforcement member 28 can be bent in accordance with rotations of the interlaced portion of the threads 29. Therefore, flexibility of the balloon 14 can be further enhanced.

As described above, the reinforcement member 28 may be formed of high-strength fibers possessing tensile break strength equal to or greater than 2 GPa and an elastic modulus equal to or greater than 50 GPa. This configuration makes it possible to form a balloon 14 having excellent high-pressure resistance and low compliance properties.

Second Embodiment

Figure 11:
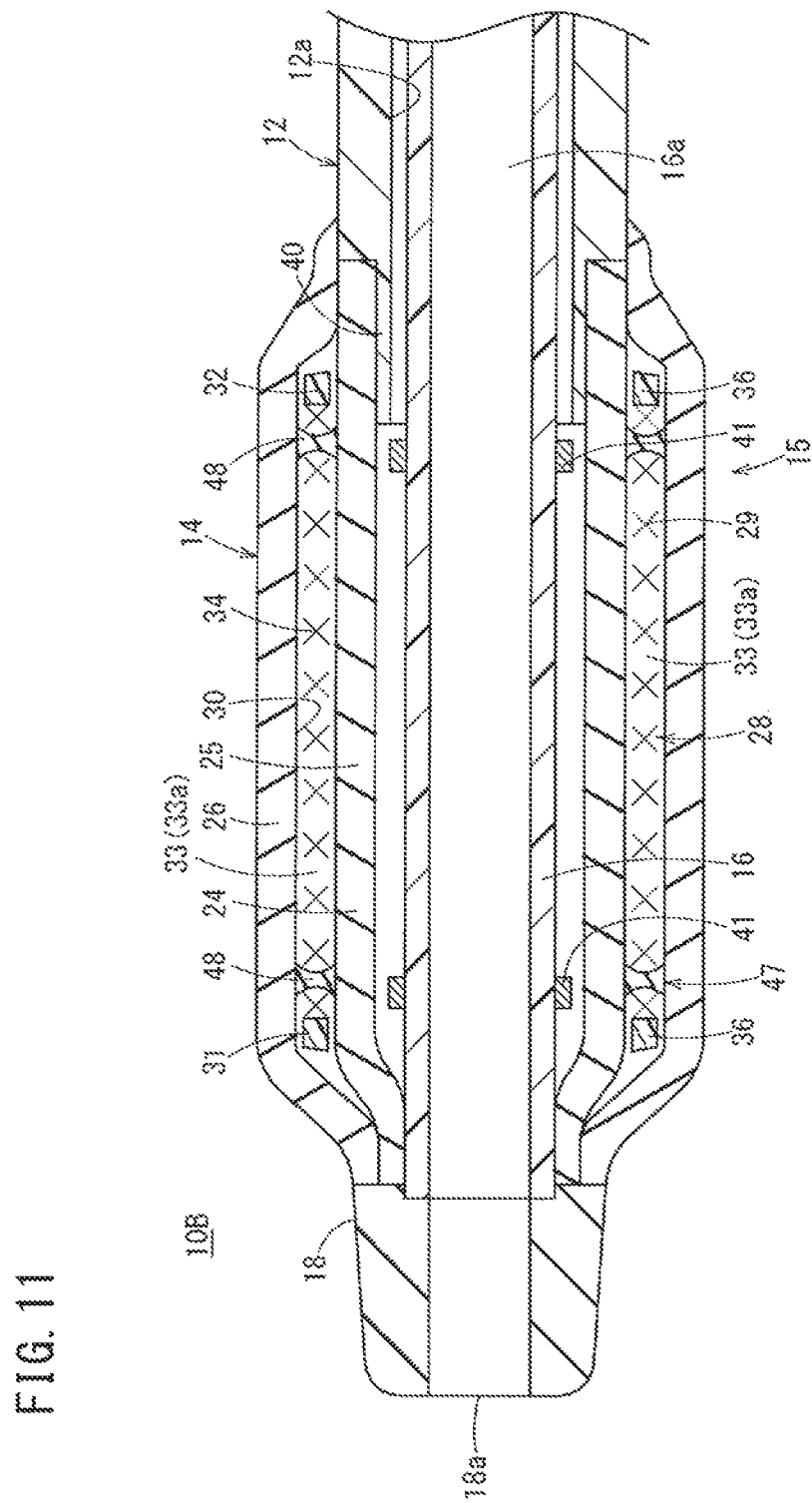
FIG. 11 is a schematic cross-sectional view of the distal portion of a catheter according to a second embodiment.

FIG. 11 illustrates a second embodiment of a catheter 10B representing another example of the catheter disclosed here. The catheter 10B illustrated in FIG. 11 includes a joint structure 47 that partially joins the inner layer 24 and the outer layer 26 to each other via a gap 33 penetrating the inner and outer surfaces of the reinforcement member 28. The joint structure 47 is not fixed to the reinforcement member 28. The joint structure 47 is provided such that the reinforcement member 28 is restrained from being misaligned in the axial direction from the initial position relative to the inner layer 24 and the outer layer 26. In the second embodiment, the gap 33 is between one thread 29 and another thread 29 configuring the reinforcement member 28 (mesh 33a).

The joint structure 47 has multiple fused portions 48 which each penetrate multiple gaps 33 (meshes 33a) of the reinforcement member 28. Each of the fused portions 48 is a portion formed after a part of the inner layer 24 and a part of the outer layer 26 are individually fused and solidified. The threads 29 configuring the reinforcement member 28 are not fused to the fused portions 48, that is, the threads 29 and the fused portions 48 are not fixed to each other. Therefore, the threads 29 are movable relative to the fused portion 48.

As illustrated in FIG. 11, the joint structure 47 (fused portion 48) is provided in only a region of the reinforcement member 28 on the first end portion 31 side and a region of the reinforcement member 28 on the second end portion 32 side. In other words, no joint structure 47 is provided between the region on the first end portion 31 side and the region on the second end portion 32 side. The region of the reinforcement member 28 on the first end portion 31 side can include not only the first end portion 31 and a part in the vicinity of the first end portion 31, but also, for example, a region to the extent of ⅓ to ¼ the overall length of the reinforcement member 28 from the outermost distal end position (i.e., distal-most end) of the reinforcement member 28. In addition, the region of the reinforcement member 28 on the second end portion 32 side can include not only the second end portion 32 and a part in the vicinity of the second end portion 32, but also a region to the extent of ⅓ to ¼ the overall length of the reinforcement member 28 from the innermost proximal end position (i.e., proximal-most end) of the reinforcement member 28.

Figure 12:
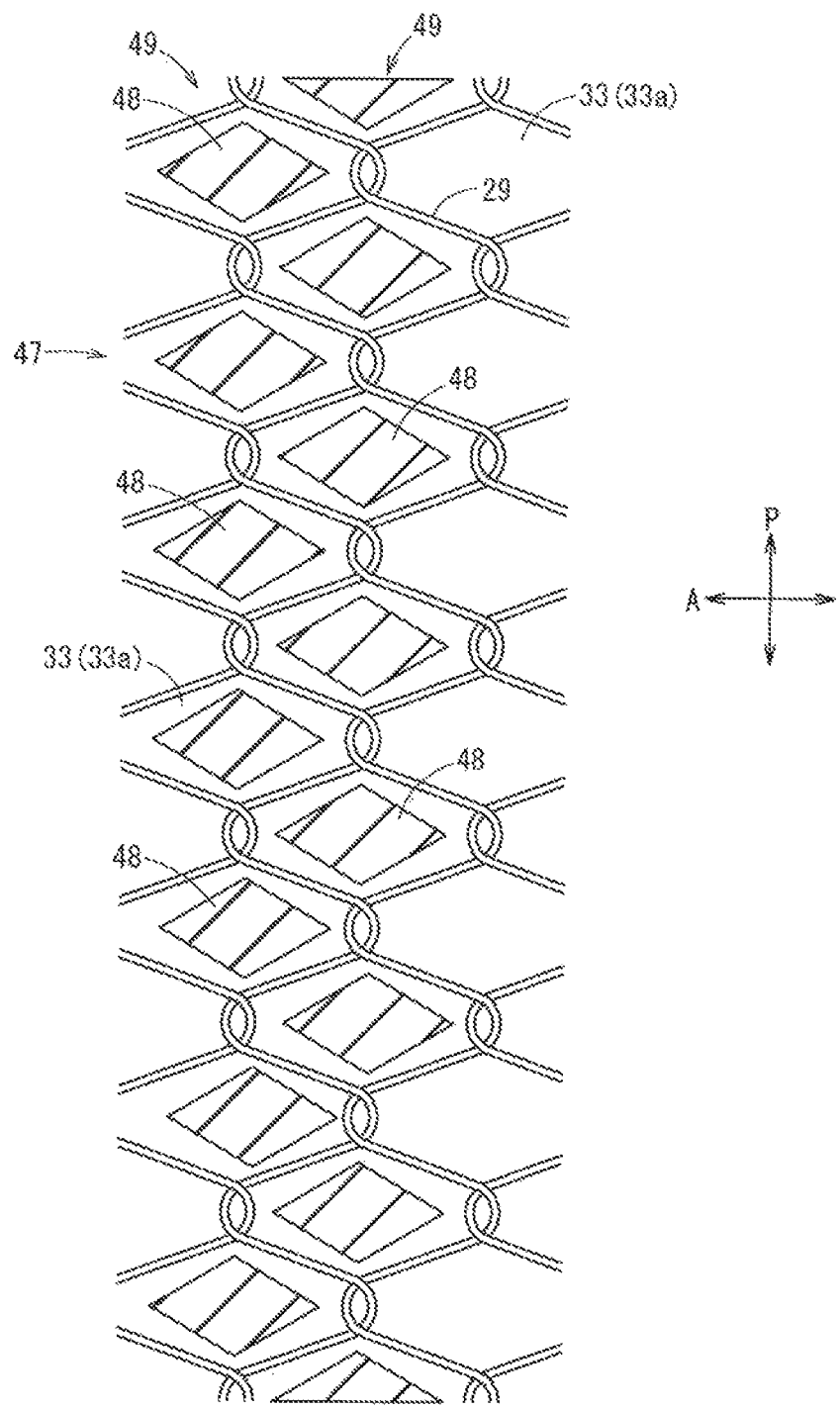
FIG. 12 is a schematic view in which a joint structure of an inner layer and an outer layer is developed in a circumferential direction.

FIG. 12 is a schematic view in which the reinforcement member 28 and the joint structure 47 (joint structure 47 on the first end portion 31 side) are developed in the circumferential direction. In FIG. 12, an arrow A direction is the axial direction, and an arrow P direction is the circumferential direction. In the present embodiment, the fused portions 48 are provided in each of the meshes 33a adjacent to each other in the circumferential direction to be spaced apart from each other in the circumferential direction. A fused portion row 49 is formed by the multiple fused portions 48 which are arranged in the circumferential direction. Multiple fused portion rows 49 are provided in the axial direction of the reinforcement member 28, and the fused portions 48 are misaligned in the circumferential direction between the fused portion rows 49. The joint structure 47 on the second end portion 32 side is also configured in a manner similar to the joint structure 47 on the first end portion 31 side.

As illustrated in FIG. 12, the thread 29 is not fixed to the fused portion 48. The space between the fused portions 48 adjacent to each other has a size equal to or greater than the thickness of the thread 29. The thread 29 is thus movable relative to the fused portion 48. The fused portion 48 is located to protrude through the gap 33 (mesh 33a) of the reinforcement member 28. Therefore, the thread 29 is caught by the fused portion 48 when the reinforcement member 28 moves. The reinforcement member 28 is thus restricted from moving in the axial direction.

The reinforcement member 28 has the appropriate degree of freedom for moving between the inner layer 24 and the outer layer 26 based on the above configuration. However, the reinforcement member 28 is not significantly misaligned in the axial direction from the initial position. Therefore, the innermost proximal end position (i.e., the proximal-most end) of the reinforcement member 28 is held on proximally beyond the stretchable region 25 of the inner layer 24. The reinforcement member 28 is thus prevented from being misaligned toward the distal side beyond the innermost proximal end position (i.e., proximal-most end) of the stretchable region 25.

The gap 33 which the fused portion 48 penetrates of the reinforcement member 28 is not limited to mesh 33a. The gap 33 may be a space other than mesh 33a. For example, the gap 33 may be a hole or a slit penetrating the inner and outer surfaces of each of the inflation restriction portions 36 on both sides of the reinforcement member 28 in the axial direction, and the fused portion 48 may be provided to penetrate the gap 33. In this embodiment, it is favorable that multiple gaps 33 in the forms of holes or slits are formed in each of the inflation restriction portions 36 to be spaced apart from each other in the circumferential direction, and so the fused portions 48 penetrate each of the gaps 33.

The portions of the catheter 10B other than the distal portion of the catheter 10B not illustrated in FIG. 11 are configured in a manner similar to the catheter 10A illustrated in FIG. 1.

Figure 13:
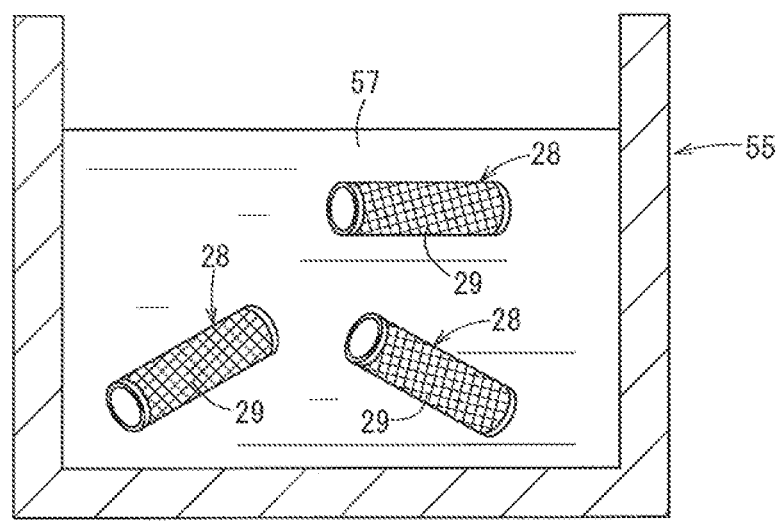
FIG. 13 illustrates a step of wetting the reinforcement member.
Figure 14A:
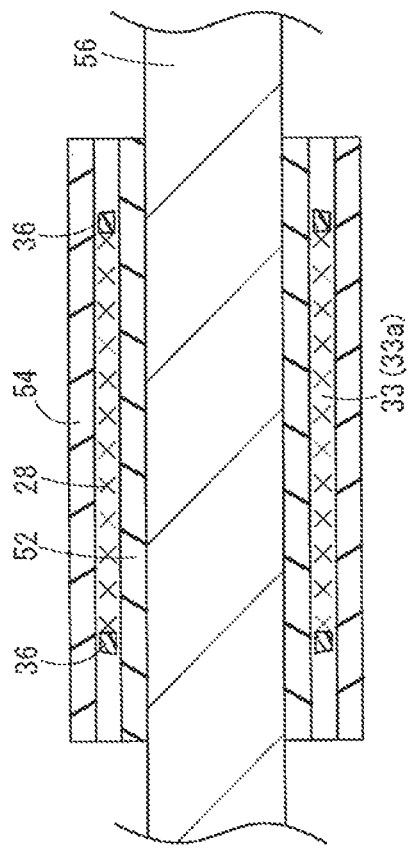
FIG. 14A illustrates forming the joint structure.
Figure 14B:
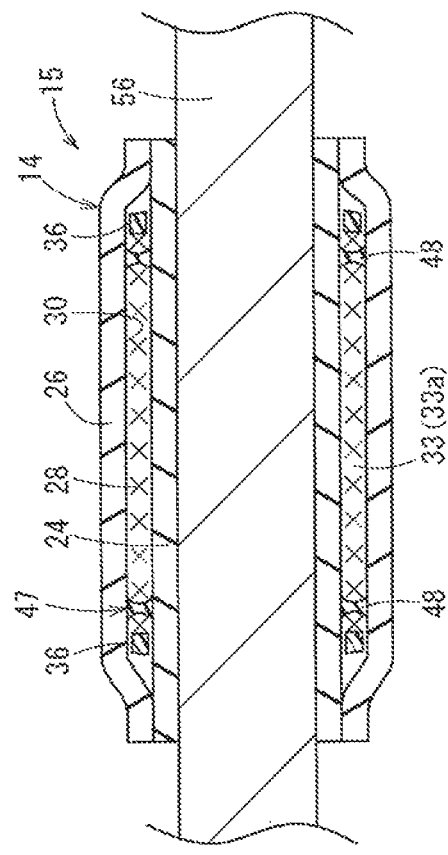
FIG. 14B is a second view illustrating forming the joint structure.

An example of a method of manufacturing the catheter 10B illustrated in FIG. 11 (mainly, the step of manufacturing the dilation portion 15 and peripheral portions of the catheter 10B) will now be described. The catheter manufacturing method of this application is not limited to the exemplified manufacturing method. In FIGS. 13, 14A, and 14B, the tubularly net-shaped reinforcement member 28 is schematically illustrated. It is not intended that the reinforcement member 28 be formed through any particular knitting method.

First, similar to the method of manufacturing the catheter 10A described above, the step of preparing a base material sleeve (FIG. 4A) and the cutting and restriction processing step (FIG. 4B) are executed to obtain multiple reinforcement members 28.

Subsequently, a step of wetting the reinforcement member 28 with liquid 57 (wetting step) is executed. The liquid 57 applied in this step is used for inhibiting the thread 29 configuring the reinforcement member 28, and the inner layer 24 and the outer layer 26 from being fused to each other in a fusing step described below. Examples of the liquid 57 include water and oil (silicone oil, and the like).

The reinforcement member 28 may be wetted in the wetting step with the liquid 57, for example as illustrated in FIG. 13, by dipping the reinforcement member 28 in the liquid 57 which is in a container 55, and then taking the reinforcement member 28 out of the liquid 57. The thread 29 configuring the reinforcement member 28 is a twisted thread formed by twisting fibers. The thread 29 thus is whetted when the liquid 57 enters between the fibers. Another method to wet the reinforcement member 28 with the liquid 57 is to apply (pour) the liquid 57 to the reinforcement member 28, spray the liquid 57 on the reinforcement member 28, paint the thread 29 with a brush, and the like. The reinforcement member 28 wetted by the liquid 57 may be obtained by knitting threads 29 (e.g., strings) which are wetted with the liquid 57 in advance.

After the reinforcement member is wetted, the method includes a disposition step of disposing the reinforcement member 28 between the inner layer 24 and the outer layer 26. For example, the disposition step includes a first covering step and a second covering step described below.

In the first covering step, similar to the method of manufacturing the catheter 10A described above, the inner layer tube 52 (which is the base material of the inner layer 24) is covered with the reinforcement member 28 wetted with the liquid 57 (refer to FIG. 5A). Note that, the reinforcement member 28 may be wetted with the liquid 57 after the inner layer tube 52 is covered with the reinforcement member 28. Subsequently, in the second covering step, similar to the method of manufacturing the catheter 10A described above, the inner layer tube 52 and the reinforcement member 28 are covered with the outer layer tube 54 (refer to FIG. 5B).

The step of joining the inner and outer layers (refer to FIGS. 6A and 6B) is then executed such that the annularly sealed accommodation chamber 30 is formed between the inner layer 24 and the outer layer 26, similar to the method of manufacturing the catheter 10A described above.

The fusing step of partially fusing the inner layer 24 and the outer layer 26 to each other via the gap 33 (mesh 33a) penetrating the inner and outer surfaces of the reinforcement member 28 is next executed without fixing the reinforcement member 28 to the inner layer 24 and the outer layer 26 as illustrated in FIGS. 14A and 14B. Portions corresponding to the first end portion 31 side and the second end portion 32 side of the reinforcement member 28 are heated by being irradiated with a laser or the like without heating the entirety of the balloon 14. The inner layer 24 and the outer layer 26 can thus be fused to each other at only the heated portions. Accordingly, the fused portion 48 can be formed in only the region on the first end portion 31 side and the region on the second end portion 32 side of the reinforcement member 28.

The reinforcement member 28 that has been wetted with the liquid 57 (refer to FIG. 13) is not fused to the inner layer 24 and the outer layer 26 during the fusing step. In other words, since the surface of the reinforcement member 28 is wet with the liquid 57, even if the reinforcement member 28 is in contact with the inner layer 24 and the outer layer 26, the materials (resin) of the inner layer 24 and the outer layer 26 do not reach or surpass the fusing point at the contact portions. As a result, the reinforcement member 28 is inhibited from being fused to the inner layer 24 and the outer layer 26.

The fused portion 48 may also be formed in the wetting step by irradiating only the spots of the meshes 33a in the reinforcement member 28 with a laser such that the inner layer 24 and the outer layer 26 are fused to each other. In this case, even though the reinforcement member 28 is not wetted with the liquid 57, the inner layer 24 and the outer layer 26 (positions in the inner layer 24 and the outer layer 26 avoiding the threads 29) can be fused to each other by selecting only the spots corresponding to the meshes 33a. When the outer layer 26 is transparent, positions of the meshes 33a in the reinforcement member 28 disposed on the inner side of the outer layer 26 can be easily checked.

This catheter manufacturing method makes it is possible to obtain the inflation portion 15 in a state where the reinforcement member 28 is movably disposed inside the accommodation chamber 30 of the balloon 14 within a restricted range. After the fusing step, the mandrel 56 is removed.

In the present embodiment, the reinforcement member 28 is merely disposed inside the accommodation chamber 30 and is not joined to other members through fusing, bonding, or the like. Therefore, the reinforcement member 28 is not fixed to any portion of the balloon 14 (inner layer 24 and outer layer 26).

Similar to the method of manufacturing the catheter 10A described above, the step of joining a balloon and a shaft (refer to FIGS. 7A and 7B), the step of fixing the radiopaque marker 41 to an inner tube, the step of joining the balloon and the inner tube (refer to FIGS. 8A and 8B), and the step of joining a distal tip and the inner tube (refer to FIGS. 9A and 9B) are sequentially executed. In the catheter manufacturing method of manufacturing the catheter 10B, steps other than those mentioned above are similar to the method of manufacturing the catheter 10A according to the first embodiment.

The catheter 10B configured as described above can perform treatment of a lesion occurring inside a body lumen by a using method similar to the catheter 10A according to the first embodiment.

High-pressure resistance and low compliance properties can be applied to the balloon 14 due to the reinforcement member 28 of the catheter 10B of this embodiment. The reinforcement member 28 has a degree of freedom for moving relative to the balloon 14. Therefore, favorable flexibility of the balloon 14 can be maintained. It is thus possible to realize the balloon 14 having high crossability inside a body lumen.

The joint structure 47 of the catheter 10B that partially joins the inner layer 24 and the outer layer 26 to each other via the gap 33 penetrating the inner and outer surfaces of the reinforcement member 28 (and that is not fixed to the thread 29 (wire member)) is provided such that the reinforcement member 28 is appropriately restrained from being misaligned in the axial direction from the initial position. Therefore, the reinforcement member 28 is not significantly misaligned in the axial direction, so that unreinforced portions of the inner layer 24 and the outer layer 26 are not exposed. The reinforcement member 28 can accordingly be suitably maintained to reinforce the balloon 14. Therefore, even after repeating the inflation and deflation of the balloon 14 multiple times, the balloon 14 does not rupture while being under low pressure. Thus, the catheter 10B can be stably used.

The joint structure 47 has one or more fused portions 48 penetrating the gaps 33 in the reinforcement member 28, and the wire member is movable relative to the fused portion 48. The thread 29 is caught by the fused portion 48 (i.e., the thread 29 is prevented from moving beyond the fused portion 48 in the axial direction) in this configuration. Therefore, the reinforcement member 28 is appropriately restrained from being misaligned. It is thus possible to simply realize a structure in which the reinforcement member 28 is effectively restrained from being misaligned in the axial direction, without fixing the reinforcement member 28 to the inner layer 24 and the outer layer 26 through the joint structure 47.

The joint structure 47 is provided in only the region of the reinforcement member 28 on the first end portion 31 side and the region of the reinforcement member 28 on the second end portion 32 side of the embodiment illustrated in FIG. 11. The reinforcement member 28 can be effectively restrained from being misaligned in the axial direction in this configuration, while maintaining favorable flexibility of the balloon 14.

The gaps 33 in the FIG. 11 embodiment are the meshes 33a in the reinforcement member 28. The meshes 33a in the reinforcement member 28 can be utilized to join the inner layer 24 and the outer layer 26 to one another, and so there is no need to provide a dedicated hole or the like in the reinforcement member 28 to join the inner layer 24 and the outer layer 26 to each other.

The catheter manufacturing method of the present embodiment results in a balloon 14 that has flexibility as well as high-pressure resistance and low compliance properties and a reinforcement member 28 that is restrained from being misaligned in the axial direction relative to the balloon 14. The catheter 10B including the balloon 14 can be manufactured so that the balloon 14 does not rupture while being under low pressure even after repeating inflation and deflation multiple times.

The catheter manufacturing method of the present embodiment includes a fusing step to heat and fuse the inner layer 24 and the outer layer 26 to one another when the reinforcement member 28 wetted with the liquid 57 is disposed between the inner layer 24 and the outer layer 26. Accordingly, the reinforcement member 28 wetted with the liquid 57 is not fused to the inner layer 24 and the outer layer 26 during this fusing step. Thus, it is possible to simply form a structure in which the reinforcement member 28 is movable relative to the inner layer 24 and the outer layer 26 even though the inner layer 24 and the outer layer 26 are partially fused to each other.

One or more regions in each of the inner layer 24 and the outer layer 26 in the axial direction are also selectively heated in the fusing step of this catheter manufacturing method embodiment. The reinforcement member 28 can thus be effectively restrained from being misaligned in the axial direction while achieving favorable flexibility of the balloon 14. To selectively heat a region in the fusing step, only a spot of the gap 33 in the reinforcement member 28 is irradiated with a laser such that the inner layer 24 and the outer layer 26 are fused to each other. Therefore, the inner layer 24 and the outer layer 26 can be fused to each other at a spot avoiding the wire member without wetting the reinforcement member 28 with the liquid 57.

Figure 15:
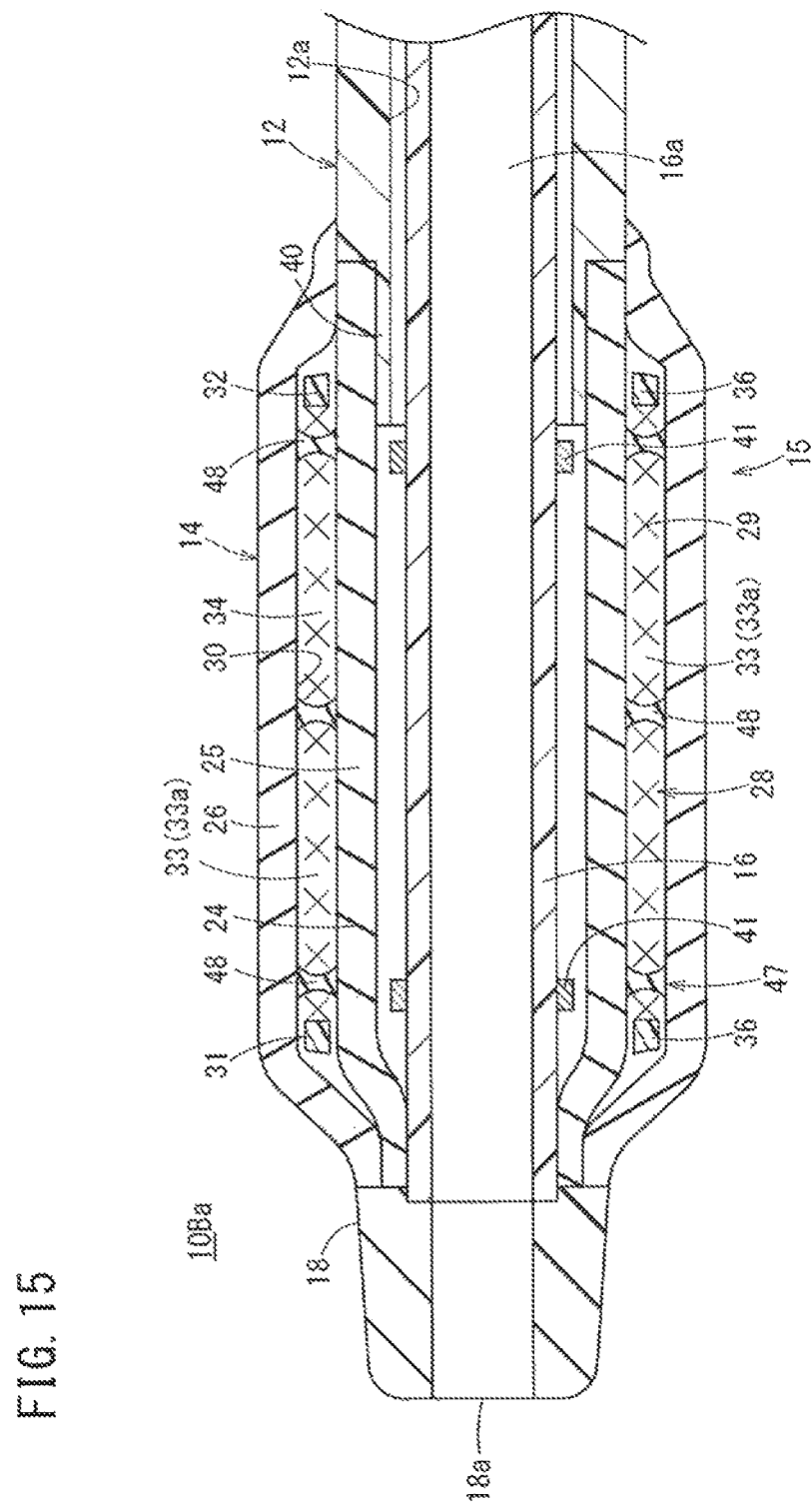
FIG. 15 is a schematic cross-sectional view of the distal portion of a catheter according to a modification example of the second embodiment.

The fused portion 48 of the catheter 10Ba may be provided in the region on the first end portion 31 side, the region on the second end portion 32 side, and a central portion of the reinforcement member 28 in the axial direction as illustrated in FIG. 15.

Figure 16:
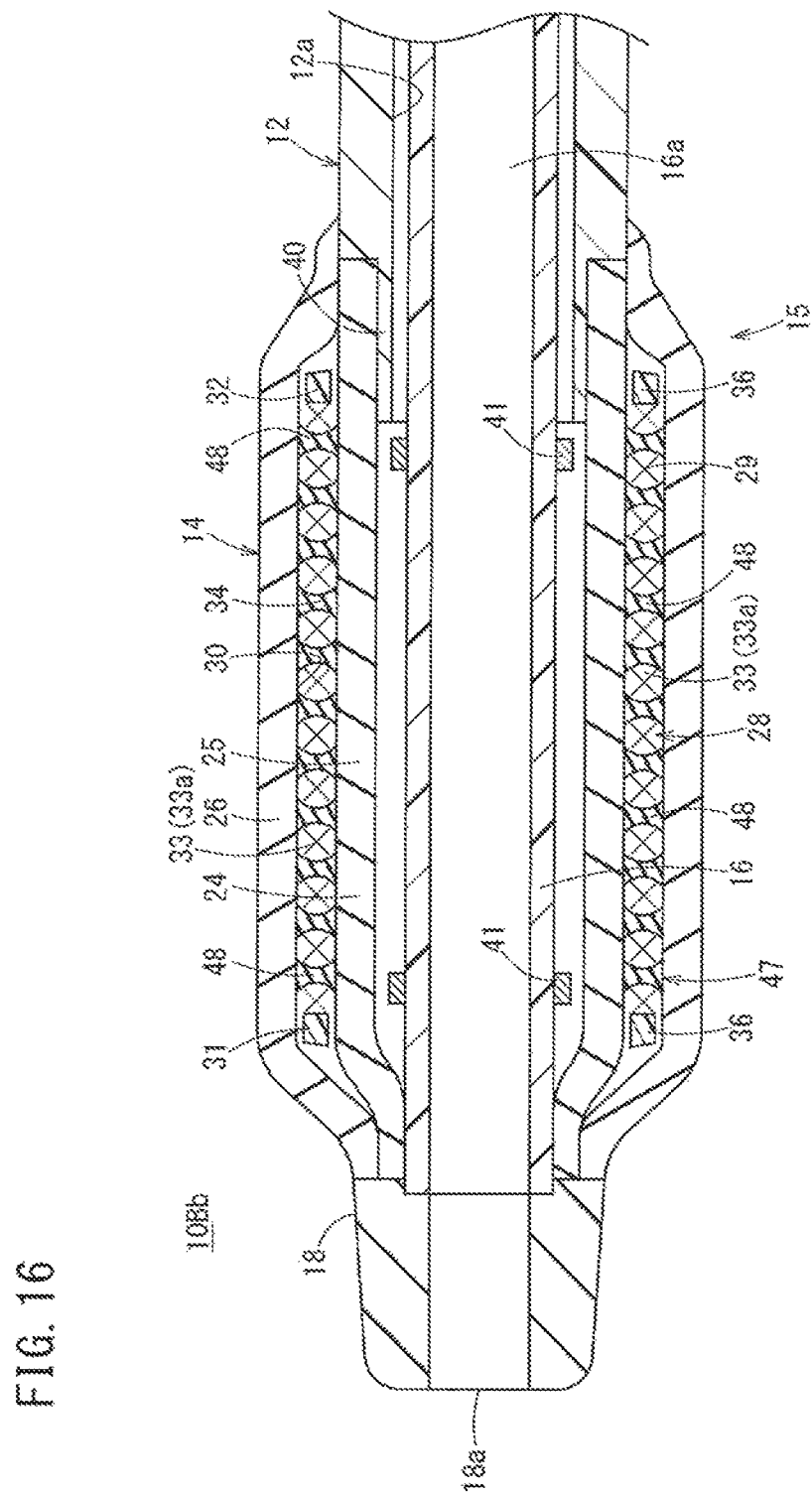
FIG. 16 is a schematic cross-sectional view of the distal portion of a catheter according to another modification example of the second embodiment.

Multiple fused portions 48 configuring the joint structure 47 of the catheter 10Bb may be disposed (while being spaced from each other) throughout substantially the entirety between the inner layer 24 and the outer layer 26 (substantially the entirety of the reinforcement member 28) as illustrated in FIG. 16. When manufacturing the catheter 10Bb, the entirety of the balloon 14 may be heated during the fusing step when the reinforcement member 28 wetted with the liquid 57 is disposed between the inner layer 24 and the outer layer 26. Accordingly, the fusing step of fusing the inner layer 24 and the outer layer 26 to each other via the gaps 33 can be efficiently carried out. The inner layer 24 and the outer layer 26 may also be fused to each other via the gap 33 by irradiating only a spot of the gap 33 in the reinforcement member 28 of the balloon 14 with a laser in the fusing step, instead of heating the entirety of the balloon 14.

The portions of the second embodiment that are common with those of the first embodiment can obtain the same or similar operations and effects as those of the first embodiment.

Third Embodiment

Figure 17:
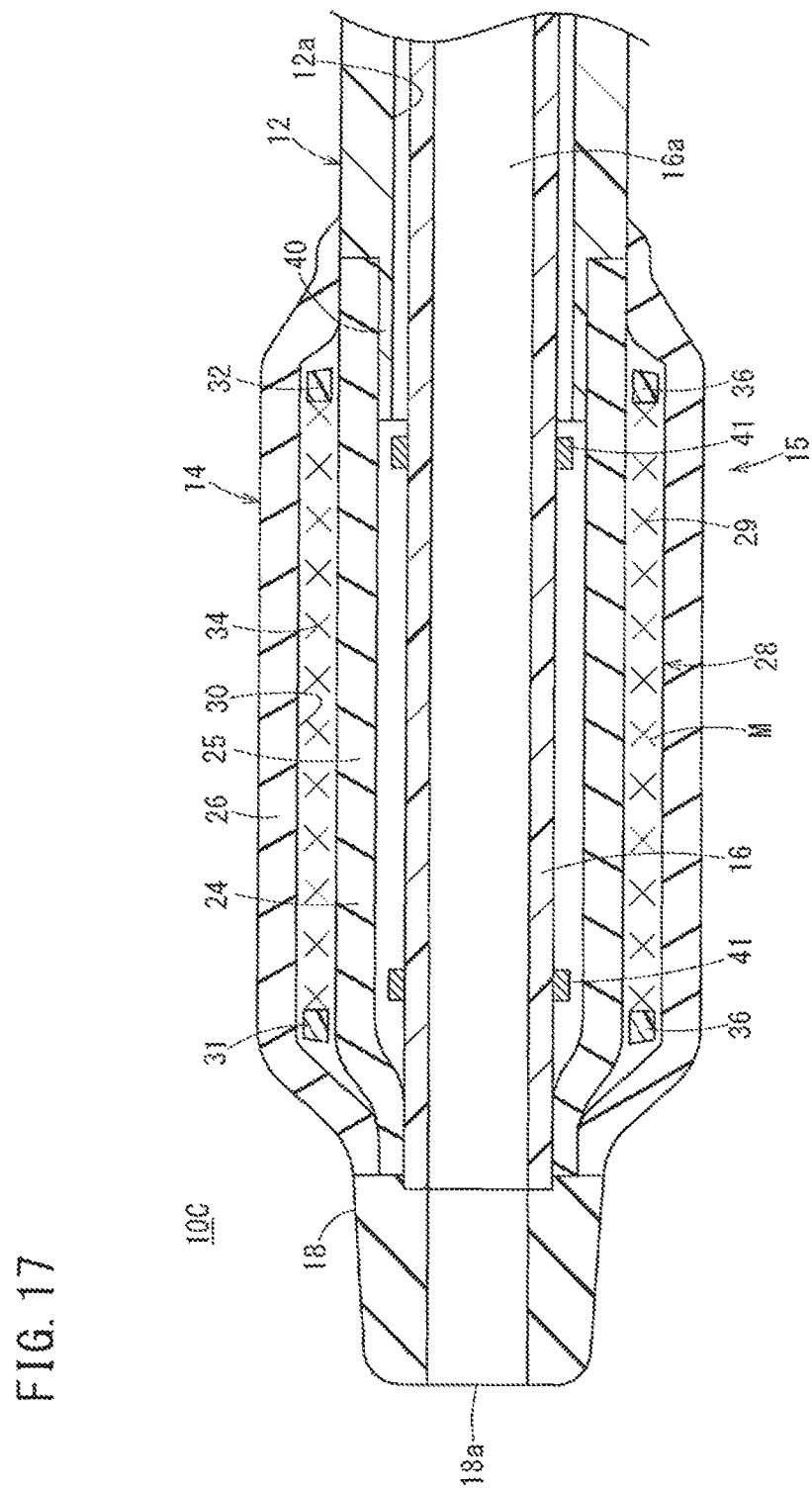
FIG. 17 is a schematic cross-sectional view of the distal portion of a catheter according to a third embodiment of the present invention.

A catheter 10C according to a third embodiment is illustrated in FIG. 17. The catheter 10C illustrated in FIG. 17 is different from the catheter 10A according to the above-described first embodiment in that a lubricant M is present on at least the outer surface of the thread 29. Specifically, the lubricant M is present on at least the outer surface of the thread 29 in the balloon 14 of the catheter 10C, such that friction between portions of the threads 29 in contact with each other (portions interlaced with each other) is reduced. In other words, movement of portions of the threads 29 that are in contact with each other becomes lubricative with each other (i.e., friction between threads 29 that contact one another decreases) due to the lubricant M.

The catheter 10C of the present embodiment has the lubricant M applied to the thread 29. The lubricant M may be any one of a liquid lubricant, a semisolid lubricant (grease), and a solid lubricant. Examples of a liquid lubricant include mineral oil, synthetic oil (silicone oil, and the like), and fatty oil. Examples of a solid lubricant include polytetrafluoroethylene. The lubricant is a substance which restrains friction or abrasion acting between two substances.

When the thread 29 is a twisted thread and the lubricant M is a liquid lubricant, the lubricant M is present not only on the outer surface of the thread 29 but also between fibers configuring the thread 29. That is, the lubricant M is in a state of being impregnated in the thread 29.

The configurations other than the distal portion of the catheter 10C not illustrated in FIG. 17 are configured in a manner similar to the catheter 10A illustrated in FIG. 1.

An example of a method of manufacturing the catheter 10C (mainly, the step of manufacturing the dilation portion 15 and peripheral portions thereof) will be next described. Note that, the catheter manufacturing method is not limited to the exemplified manufacturing method.

The method of manufacturing the catheter 10C further includes a step of applying the lubricant M to the thread 29 (fibers) configuring the reinforcement member 28 (applying step) (i.e., a further step compared to the method of manufacturing the catheter 10A according to the first embodiment (refer to FIGS. 4A to 9B)). This applying step is executed between the cutting and restriction processing step (refer to FIG. 4B) to form the inflation restriction portion 36 at both the end portions of the divided sleeve 51, and the first covering step (refer to FIG. 5A) covering the inner layer tube 52 with the reinforcement member 28.

Figure 18:
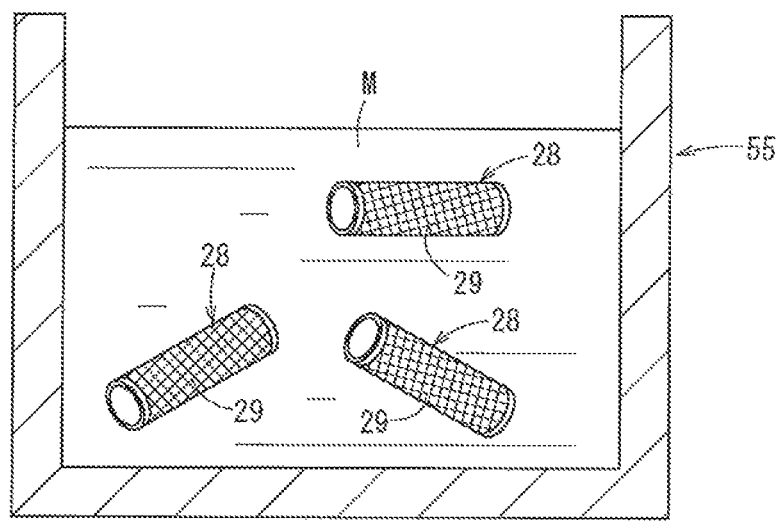
FIG. 18 is a view describing a step of applying a lubricant to threads configuring the reinforcement member.

When the lubricant M is liquid, for example as illustrated in FIG. 18, the lubricant M may be applied to the reinforcement member 28 in the applying step by dipping the reinforcement member 28 in the lubricant M which is in the container 55 and then taking out the reinforcement member 28. The thread 29 configuring the reinforcement member 28 is a twisted thread which is formed by twisting fibers. Therefore, when the lubricant M enters between the fibers, the lubricant M is impregnated in the thread 29. As another method, the lubricant M may be applied to the reinforcement member 28 by applying (pouring) the lubricant M, spraying the lubricant M, painting the reinforcement member 28 with a brush, and the like. The reinforcement member 28 in which the lubricant M is applied to the thread may also be obtained by applying the lubricant M in advance to the thread 29 and then knitting the thread 29 into the reinforcing member 28.

The catheter 10C configured as described above can perform treatment of a lesion occurring inside a body lumen by a using method similar to the methods described above regarding the catheter 10A according to the first embodiment.

In the catheter 10C according to the present embodiment, the lubricant M is present on at least the outer surface of the thread 29 (wire member) such that friction between the threads 29 (portions of the threads 29 in contact with each other) is reduced. Friction between the threads 29 can be reduced in this configuration, and the degree of freedom of movement between the threads 29 can be enhanced because the lubricant M makes the threads 29 lubricative relative to one another. Thus, when being deflated again after inflation, the balloon 14 can easily restore the original shape (the thickness) before being inflated.

Since the lubricant M is applied to the threads 29, the amount of the using lubricant M can be restrained, and friction between the portions of the thread 29 in contact with each other can be efficiently reduced.

The reinforcement member 28 of this embodiment is formed of high-strength fibers of which tensile break strength is equal to or greater than 2 GPa and an elastic modulus is equal to or greater than 50 GPa. According to the configuration, it is possible to realize the balloon 14 having excellent high-pressure resistance and low compliance properties.

Generally, frictional resistance between high-strength fibers (super fibers) is relatively high. Therefore, when the reinforcement member 28 is configured with the high-strength fiber, if the fibers are in direct contact with each other without being lubricated, there is a possibility that when the balloon 14 is deflated again, it may be difficult for the balloon 14 to restore the original shape before being inflated. In contrast, when the lubricant M is present on the outer surface of the thread 29 formed of the high-strength fiber is employed as in the present embodiment, a problem of frictional resistance occurring when a high-strength fiber is used as the thread 29 can be restrained (reduced), and high-pressure resistance and low compliance properties can be effectively applied to the balloon 14.

Figure 19:
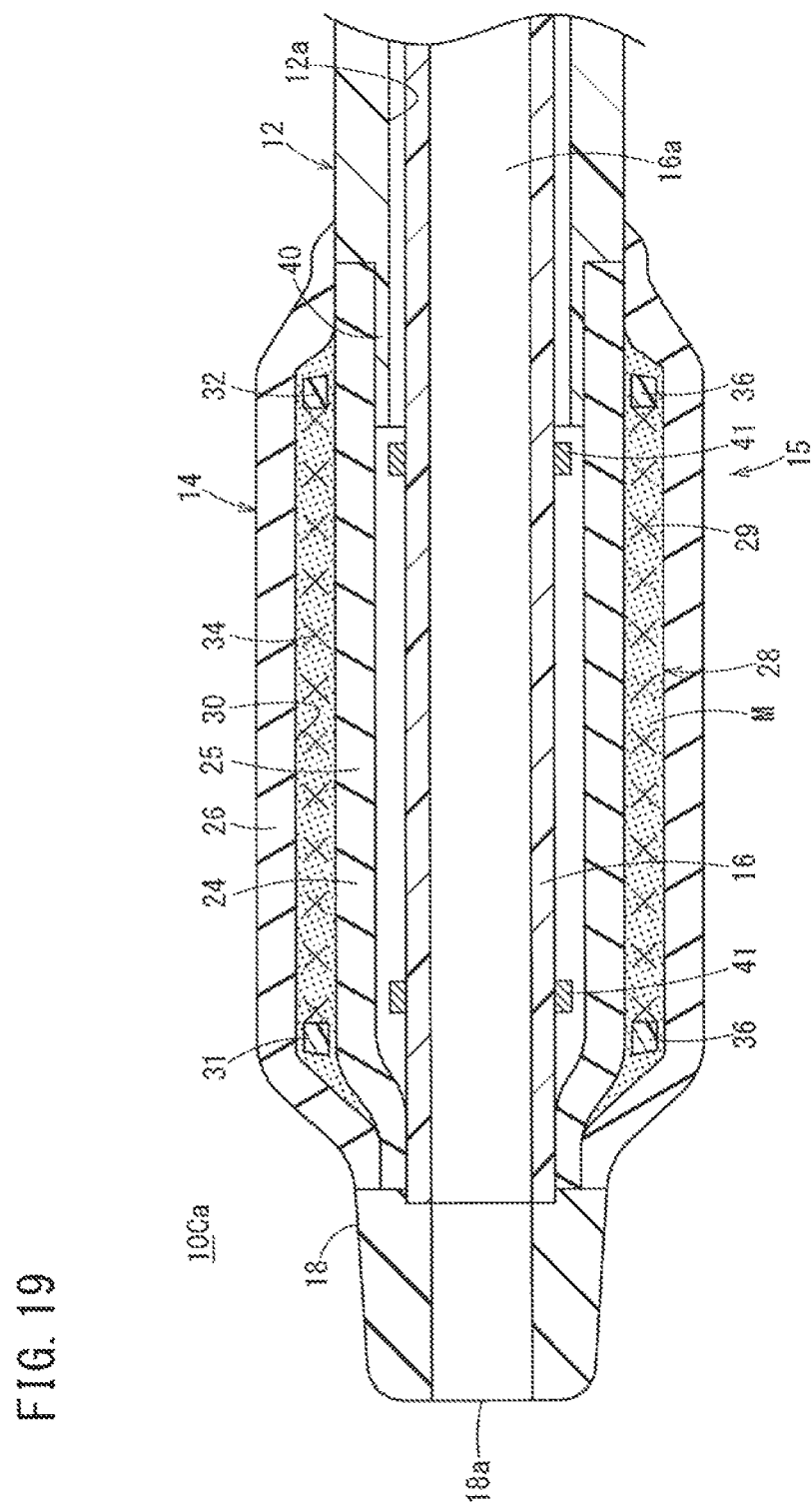
FIG. 19 is a schematic cross-sectional view of the distal portion of a catheter according to a modification example of the third embodiment.

FIG. 19 is a schematic cross-sectional view of the distal portion of a catheter 10Ca according to a modification example of the third embodiment. In the catheter 10Ca, the accommodation chamber 30 formed between the inner layer 24 and the outer layer 26 is filled with the lubricant M. The lubricant M is in a liquefied state or a semisolid state. This configuration can help ensure that lubricant M is present around the thread 29 configuring the reinforcement member 28. Therefore, friction between the portions of the threads 29 in contact with each other can be reliably reduced. The lubricant M does not leak out from the balloon 14 because the accommodation chamber 30 is a sealed space.

In the third embodiment, regarding the common portions of the first embodiment, the operations and the effects which are the same as or similar to those of the first embodiment can be obtained.

The detailed description above describes a catheter and a catheter manufacturing method. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:
1. A catheter comprising:
a balloon extending in an axial direction and comprising an elastic inner layer and an elastic outer layer, the inner and outer layers being tubular and being inflatable and deflatable in a radial direction in response to a change of internal pressure of the balloon;
a tubular reinforcement member positioned between the inner layer and the outer layer in the radial direction;
the reinforcement member comprising a first end portion and a second end portion opposite the first end portion in the axial direction, the reinforcement member comprising an intermediate portion between the first end portion and the second end portion in the axial direction;

at least one of the first end portion and the second end portion being not directly fixed to the inner layer and the outer layer; and the intermediate portion being not directly fixed to the inner layer and not directly fixed to the outer layer.

2. The catheter according to claim 1, wherein both the first end portion and the second end portion are not directly fixed to the inner layer and are not directly fixed to the outer layer.

3. The catheter according to claim 1, wherein inflation of the first end portion and the second end portion in the radial direction is restricted.

4. The catheter according to claim 1, wherein
the reinforcement member is a tubularly knitted member of one or more wave-shaped threads, and
the wave-shaped threads adjacent to each other in the axial direction are interlaced with each other.

5. The catheter according to claim 1, wherein the reinforcement member is a fiber possessing a tensile break strength equal to or greater than 2 GPa and an elastic modulus equal to or greater than 50 GPa.

6. The catheter according to claim 1, wherein
the inner layer comprises a stretchable region that is stretchable during inflation and deflation of the balloon, the stretchable region possessing a length in the axial direction,
the outer layer possesses a length in the axial direction,
the reinforcement member possesses a length in the axial direction,
the length of the reinforcement member in the axial direction is greater than the length of the stretchable region of the inner layer in the axial direction, and
the length of the outer layer in the axial direction is greater than the length of the reinforcement member in the axial direction.

7. The catheter according to claim 1, wherein
the reinforcement member possesses an inner surface and an outer surface, the reinforcement member comprising multiple gaps penetrating through the inner surface and the outer surface of the reinforcement member,
the catheter further comprising a joint structure that partially joins the inner layer and the outer layer to each other via the multiple gaps penetrating the inner and outer surfaces of the reinforcement member, the joint structure being positioned so that the reinforcement member is restrained from being misaligned in the axial direction with respect to the balloon, and
the joint structure not being fixed to the reinforcement member so that the reinforcement member is movable relative to the balloon.

8. The catheter according to claim 7, wherein
the joint structure comprises multiple fused portions penetrating the multiple gaps, and
the reinforcement member is movable relative to the fused portions.

9. The catheter according to claim 7, wherein the joint structure is provided in only a first region of the reinforcement member near the first end portion and a second region of the reinforcement member near the second end portion.

10. The catheter according to claim 7, wherein the reinforcement member is mesh and the multiple gaps of the reinforcement member are gaps in the mesh.

11. The catheter according to claim 1, wherein
the reinforcement member comprises one or more wire members, the one or more wire members possessing outer surfaces, and
a lubricant is present on at least the outer surfaces of the one or more wire members to reduce friction between portions of outer surfaces of the one or more wire members that contact each other.

12. The catheter according to claim 1, wherein the reinforcement member includes multiple gaps spaced apart from one another and penetrating through the reinforcement member, the inner layer of the balloon and the outer layer of the balloon being fused to each other at fused portions each located at one of the gaps.

13. The catheter according to claim 1, wherein the inner layer of the balloon and the outer layer of the balloon are fused to each other at a plurality of spaced apart fused portions that pass through the reinforcement member, the reinforcement member being movable relative to the inner and outer layers of the balloon at the fused portions.

14. The catheter according to claim 1, wherein the reinforcement member is comprised of one or more woven threads so that the reinforcement member includes a plurality of spaced apart gaps that pass through the reinforcement member.

15. The catheter according to claim 1, wherein the inner layer of the balloon and the outer layer of the balloon are made of the same material.

16. The catheter according to claim 1, further comprising an elongated shaft possessing a distal-most end portion, the distal-most end portion of the elongated shaft possessing a thickness that is reduced relative to an immediately adjacent portion of the elongated shaft, a proximal-most end portion of the inner layer of the balloon being joined to an outer surface of the distal-most end portion of the elongated shaft possessing the thickness that is reduced relative to the immediately adjacent portion of the elongated shaft, a proximal-most end portion of the outer layer of the balloon axially overlying the immediately adjacent portion of the elongated shaft.

17. A catheter comprising:
an elongated shaft extending in an axial direction;
a balloon connected to the shaft, the balloon comprising a tubular elastic inner layer and a tubular elastic outer layer, the inner and outer layers being inflatable and deflatable in response to a change of internal pressure of the balloon, the outer layer possessing an inner surface and the inner layer possessing an outer surface;
at least a portion of the inner surface of the outer layer being spaced radially outwardly from at least a portion of the outer surface of the inner layer;
an accommodation chamber formed by the portion of the inner surface of the outer layer spaced radially outwardly from the portion of the outer surface of the inner layer;
a reinforcement member positioned in the accommodation chamber, the reinforcement member comprising a first end portion and a second end portion opposite the first end portion in the axial direction, the reinforcement member comprising an intermediate portion located between the first end portion and the second end portion in the axial direction;
the reinforcement member comprising a plurality of spaced apart gaps that pass through the reinforcement member; and
the inner layer of the balloon and the outer layer of the balloon being fused to each other at a plurality of spaced apart fused portions each located at one of the gaps.

18. The catheter according to claim 17, wherein the accommodation chamber is filled with lubricant.

19. The catheter according to claim 17, wherein
the reinforcement member is a tubular mesh formed by a fiber which possesses a tensile break strength equal to or greater than 2 GPa and an elastic modulus equal to or greater than 50 GPa;
the first end portion is movable relative to both the inner layer and the outer layer; and
the intermediate portion is movable relative to both the inner layer and the outer layer.

20. A catheter comprising:
a balloon extending in an axial direction and comprising an elastic inner layer and an elastic outer layer, the inner and outer layers being tubular and being inflatable and deflatable in a radial direction in response to a change of internal pressure of the balloon;
a tubular reinforcement member positioned between the inner layer and the outer layer in the radial direction;
the reinforcement member comprising a first end portion and a second end portion opposite the first end portion in the axial direction, the reinforcement member comprising an intermediate portion between the first end portion and the second end portion in the axial direction;
at least one of the first end portion and the second end portion being not directly fixed to the inner layer and the outer layer;
the intermediate portion being not directly fixed to the inner layer and are not directly fixed to the outer layer;
the reinforcement member possessing an inner surface and an outer surface, the reinforcement member comprising multiple gaps penetrating through the inner surface and the outer surface of the reinforcement member,
the catheter further comprising a joint structure that partially joins the inner layer and the outer layer to each other via the multiple gaps penetrating the inner and outer surfaces of the reinforcement member, the joint structure being positioned so that the reinforcement member is restrained from being misaligned in the axial direction with respect to the balloon, and
the joint structure not being fixed to the reinforcement member so that the reinforcement member is movable relative to the balloon.

* * * * *